United States Patent
Oshiumi

(10) Patent No.: US 9,908,889 B2
(45) Date of Patent: Mar. 6, 2018

(54) SALT OF FUSED PYRIMIDINE COMPOUND AND CRYSTAL THEREOF

(71) Applicant: TAIHO PHARMACEUTICAL CO., LTD., Chiyoda-ku (JP)

(72) Inventor: Hiromi Oshiumi, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 15/297,180

(22) Filed: Oct. 19, 2016

(65) Prior Publication Data

US 2017/0044166 A1    Feb. 16, 2017

Related U.S. Application Data

(63) Continuation of application No. PCT/JP2016/052733, filed on Jan. 29, 2016.

(30) Foreign Application Priority Data

Jan. 30, 2015 (JP) .................................. 2015-017387

(51) Int. Cl.
*C07D 487/04* (2006.01)
*A61K 31/519* (2006.01)

(52) U.S. Cl.
CPC .......... *C07D 487/04* (2013.01); *A61K 31/519* (2013.01)

(58) Field of Classification Search
CPC ............................. C07D 487/04; A61K 31/519
See application file for complete search history.

(56) References Cited

U.S. PATENT DOCUMENTS

| 8,673,925 B1 | 3/2014 | Goldstein |
| 2014/0336203 A1 | 11/2014 | Smyth et al. |
| 2016/0115168 A1 | 4/2016 | Iguchi et al. |

FOREIGN PATENT DOCUMENTS

| EP | 2947086 | 11/2015 |
| WO | WO 2009/158571 A1 | 12/2009 |
| WO | WO 2011/090760 A1 | 7/2011 |
| WO | WO 2013/184572 A1 | 12/2013 |
| WO | WO 2015/022926 A1 | 2/2015 |
| WO | WO2016121953 | * 8/2016 |

OTHER PUBLICATIONS

Bhattacharya et al. (Brittain, ed. Polymorphism in Pharmaceutical Solids, 2009, p. 334.*
Berge (J. of Pharmaceutical Sciences, 1977, 66(1), pp. 1-19).*
International Search Report dated Apr. 19, 2016, in PCT/JP2016/052733, filed Jan. 29, 2016.
Current Opinion in Immunology, Jun. 2000; 12(3): 282-288.
Proc. Natl. Acad. Sci. USA., Jul 20, 2010; 107(29):13075-80.
Nature Rev. Cancer, vol. 6, pp. 803-811 (2006).
Nature Rev. Clin. Oncol., vol. 6, pp. 98-109 (2012).
American College of Rheumatology Annual Meeting, Atlanta, GA, Nov. 6-11, 2010).
European Search Report dated Jan. 30, 2017, in European Patent Application No. 16743557.7.

* cited by examiner

*Primary Examiner* — Susanna Moore
(74) *Attorney, Agent, or Firm* — Oblon, McClelland, Maier & Neustadt, L.L.P.

(57) ABSTRACT

Provided is a salt having a high selectivity to BTK and is useful as a drug ingredient for a pharmaceutical product.
It has been found that fumarate of Compound A is free of a characteristic of channel hydrate and is stable and excellent in absorptive property, compared to Compound A or other salts thereof.

15 Claims, 11 Drawing Sheets

SALT OF FUSED PYRIMIDINE COMPOUND AND CRYSTAL THEREOF

TECHNICAL FIELD

The present invention relates to a novel salt of a compound having an inhibitory activity against Bruton's tyrosine kinase (BTK), and a crystal thereof.

BACKGROUND ART

It is known that various protein kinases exist in vivo and are involved in the regulation of a variety of functions. Bruton's tyrosine kinase (BTK) is a protein kinase that belongs to the Tec family kinases, and is a non-receptor tyrosine kinase that plays an important role related to the control of, for example, proliferation, survival, differentiation and activation of B-cells in the downstream of the B cell receptor (BCR) signal (Non-Patent Literature 1). An inhibitor capable of controlling the BTK activity is considered to be useful as a therapeutic agent for diseases associated with abnormal hyperactivity of BTK signaling pathway (for example, cancer).

Regarding a compound having BTK inhibitory activity, PCI-32765 (Non-Patent Literature 2) and the compounds described in Patent Literatures 1 and 2 are known.

The compounds disclosed in Patent Literatures 1 and 2 are also known to exhibit high inhibitory activity for EGFR (Epidermal Growth Factor Receptor) and JAK3 (Janus kinase 3) for example, in addition to BTK. However, since such a multikinase inhibitor suppresses, for example, cell proliferation by inhibiting various signaling pathways, there is a concern about a variety of adverse effects. For example, it is known that EGFR binds to its ligand, for example, the epidermal growth factor (EGF), and participates in the proliferation and survival (for example, inhibition of apoptosis) of various cells (Non-Patent Literature 3). However, it is known that inhibitors targeting EGFR cause adverse effects such as skin disorders and gastrointestinal dysfunction in common, and it is widely supposed that these adverse effects may be related to the inhibition of the wild type EGFR signaling pathway (Non-Patent Literature 4).

Thus, PCI-45292 is known as a compound, which has an inhibitory activity against BTK with a weak inhibitory activity against EGFR (Non-Patent Literature 5).

CITATION LIST

Patent Literatures

Patent Literature 1: WO 2011/090760
Patent Literature 2: WO 2009/158571

Non-Patent Literatures

Non-Patent Literature 1: Curr. Opin. Immunol., 2000 June; 12(3): 282-8
Non-Patent Literature 2: Proc. Natl. Acad. Sci. USA, 2010 Jul. 20; 107(29):13075-80
Non-Patent Literature 3: Nature Rev. Cancer, Vol. 6, pp. 803-811 (2006)
Non-Patent Literature 4: Nature Rev. Clin. Oncol., Vol. 6, pp. 98-109 (2012)
Non-Patent Literature 5: American College of Rheumatology Annual Meeting, Atlanta, Ga., 6-11 Nov. 2010)

SUMMARY OF INVENTION

Technical Problem

An object of the present invention is to provide a salt which is a BTK inhibitor with a high selectivity, having a high inhibitory activity against BTK and a low inhibitory activity against other kinases such as EGFR, and which is useful as a drug ingredient for a pharmaceutical product.

Solution to Problem

As a result of earnest research to solve the problem, the present applicant has found that (R)-1-(1-acryloylpiperidin-3-yl)-4-amino-N-(benzo[d]oxazol-2-yl)-1H-pyrazolo[3,4-d]pyrimidine-3-carboxamide (Compound A) represented by the following formula (1) has a high inhibitory activity against BTK, with having a low inhibitory activity against other kinases such as EGFR, and is useful as a medicine for treating cancers, autoimmune diseases, or allergic diseases.

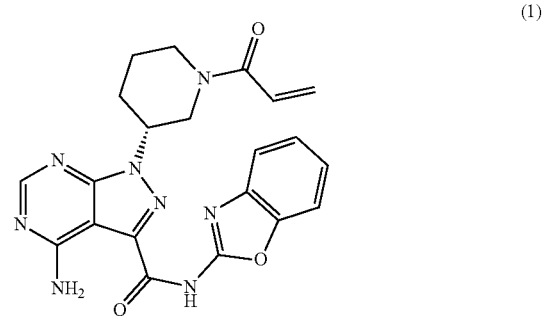 [SMILES: C=CC(=O)N1CCC[C@@H](n2nc(C(=O)Nc3nc4ccccc4o3)c3c(N)ncnc32)C1]

(1)

Then, during a research of physicochemical properties of Compound A for the purpose of development of a formulation of Compound A, the present applicant has found that (1) Compound A is hard to use as a drug ingredient for a pharmaceutical product, for having a characteristic as a channel hydrate of absorbing moisture in the air when a free form of Compound A is exposed to an atmosphere of high humidity, and discharging moisture when exposed to an atmosphere of low humidity, (2) an acid addition salt is produced only with tartaric acid, phosphoric acid, or fumaric acid, with regard to an acid addition salt of Compound A, and (3) even more surprisingly, among these acid addition salts, only fumarate is free of the characteristic of channel hydrate, and has accomplished the present invention.

More specifically, in an industrial production of a pharmaceutical product, it is required that a drug ingredient have stability, etc. However, the stability, etc. depend on the attribute of each compound. Therefore, in a complex compound, it is difficult to predict a salt having appropriate properties as a drug ingredient for a pharmaceutical product, and accordingly, it is desired to find out, for each compound, various salts which are useful for pharmaceutical products. From such a point of view, the present applicant has synthesized various salts of Compound A and has researched properties, stability, etc. thereof. As a result, our research succeeded in forming a salt of a fumarate, a tartrate, a phosphate and a magnesium salt. However, among these salts and a free form, the tartrate and the free form had the characteristic of channel hydrate and a poor solid stability; the phosphate failed to maintain its original crystal form in a moisture absorption/desorption test, and in addition, had a poor solid stability; and the magnesium salt had a low crystal purity, for including a lot of analogous substances. It was found that only the fumarate could avoid the characteristic of channel hydrate, and at the same time, was excellent in obtaining-operability and reproducibility, and stable and excellent in absorptive property, and thus, the present invention has been accomplished.

That is, the present invention relates to the following 1) to 18).

1) Fumarate of (R)-1-(1-acryloylpiperidin-3-yl)-4-amino-N-(benzo[d]oxazol-2-yl)-1H-pyrazolo[3,4-d]pyrimidine-3-carboxamide (Compound A).
2) (R)-1-(1-acryloylpiperidin-3-yl)-4-amino-N-(benzo[d]oxazol-2-yl)-1H-pyrazolo[3,4-d]pyrimidine-3-carboxamide (Compound A).hemifumarate.
3) (R)-1-(1-acryloylpiperidin-3-yl)-4-amino-N-(benzo[d]oxazol-2-yl)-1H-pyrazolo[3,4-d]pyrimidine-3-carboxamide (Compound A).monofumarate.
4) A BTK inhibitor containing the fumarate of Compound A as an active ingredient.
5) A pharmaceutical composition containing the fumarate of Compound A.
6) An anti-tumor agent or a preventive and/or therapeutic agent of allergic diseases, autoimmune diseases or inflammatory diseases containing the fumarate of Compound A as an active ingredient.
7) A anti-tumor agent against a hematologic tumor or a preventive and/or therapeutic agent of allergic rhinitis, pollinosis, atopic dermatitis, rheumatoid arthritis or systemic lupus erythematosus, which contains the fumarate of Compound A as an active ingredient.
8) Use of the fumarate of Compound A for producing a BTK inhibitor.
9) Use of the fumarate of Compound A for producing a pharmaceutical composition.
10) Use of the fumarate of Compound A for producing an anti-tumor agent or a preventive and/or therapeutic agent of allergic diseases, autoimmune diseases or inflammatory diseases.
11) Use of the fumarate of Compound A for producing an anti-tumor agent against a hematologic tumor or a preventive and/or therapeutic agent of allergic rhinitis, pollinosis, atopic dermatitis, rheumatoid arthritis or systemic lupus erythematosus.
12) The fumarate of Compound A for use in a BTK inhibition.
13) The fumarate of Compound A for use as a medicine.
14) The fumarate of Compound A for use in a preventive and/or therapeutic agent of a tumor, an allergic disease, an autoimmune disease or an inflammatory disease.
15) The fumarate of Compound A for use in prevention or treatment of a hematologic tumor, allergic rhinitis, pollinosis, atopic dermatitis, rheumatoid arthritis or systemic lupus erythematosus.
16) A method of inhibiting BTK, containing administering an effective amount of the fumarate of Compound A to a subject in need thereof.
17) A method of preventing and/or treating a tumor, an allergic disease, an autoimmune disease or an inflammatory disease containing administering an effective amount of the fumarate of Compound A to a subject in need thereof.
18) A method of treating a hematologic tumor, allergic rhinitis, pollinosis, atopic dermatitis, rheumatoid arthritis or systemic lupus erythematosus, containing administering an effective amount of the fumarate of Compound A to a subject in need thereof.

Advantageous Effects of Invention

The fumarate of Compound A of the present invention has an excellent solid stability as a drug ingredient for a pharmaceutical product, and is capable of avoiding the characteristic of channel hydrate, compared to Compound A or salts other than the fumarate of Compound A, and excellent in obtaining-operability and reproducibility. Moreover, the fumarate of Compound A of the present invention exhibits an excellent oral absorption property, and is extremely useful as a pharmaceutical product or as a drug ingredient for a pharmaceutical product.

DESCRIPTION OF EMBODIMENTS

Hereinbelow, the present invention will be described in detail.

"Compound A" simply described in the present specification refers to (R)-1-(1-acryloylpiperidin-3-yl)-4-amino-N-(benzo[d]oxazol-2-yl)-1H-pyrazolo[3,4-d]pyrimidine-3-carboxamide in free form.

"Fumarate of Compound A" simply described in the present specification may be any one of salt forms of Compound A with fumaric acid, involving monofumarate and hemifumarate. The term is further used in a meaning involving both a crystal of fumarate of Compound A and an amorphous of fumarate of Compound A. The fumarate of Compound A is preferably monofumarate of Compound A (which may be abbreviated as "Compound A-monofumarate") and hemifumarate of Compound A (which may be abbreviated as "Compound A-hemifumarate"); more preferably monofumarate of Compound A (crystal), hemifumarate of Compound A (crystal) and monofumarate of Compound A (amorphous); and particularly preferably monofumarate of Compound A (crystal) and hemifumarate of Compound A (crystal).

In the present specification, the terms "crystal" and "amorphous" are used in usual meanings.

Multiple crystal forms which are different from one another in spatially orderly atomic arrangement and in physicochemical properties (polymorphisms) occur in some cases. The salt of the present invention may be any one of these polymorphisms, and may be a mixture of two or more polymorphisms, or a mixture of a crystal and an amorphous.

The present invention also involves a labeled form of fumarate of Compound A, that is, a compound having one or more atoms of Compound A or a fumarate substituted with a radioisotopic element or a non-radioisotopic element.

In this connection, in a powder X-ray diffraction spectrum, a diffraction angle or a general pattern are important in recognizing an identity of crystals, for a nature of data. Relative intensity of a powder X-ray diffraction spectrum can slightly vary depending on direction of crystal growth, size of particles, or condition of measurement, and therefore, should not be strictly interpreted.

A numerical value obtained from various patterns may be accompanied by a slight error due to the direction of crystal growth, size of particles, or condition of measurement thereof. Therefore, in the present specification, the term diffraction angle (2θ+0.1°) in the powder X-ray diffraction spectrum refers to a value which may be in a range within ±0.1° of a value.

The term "in the vicinity" which is used with a peak temperature of an endothermic peak in a differential scanning calorie (DSC) curve refers to a value which approximately is the temperature, preferably refers to a value which may be within a range of ±5° C. of the value. More preferably, it refers to a value which may be in a range within ±2° C. of the value.

Figure 4:
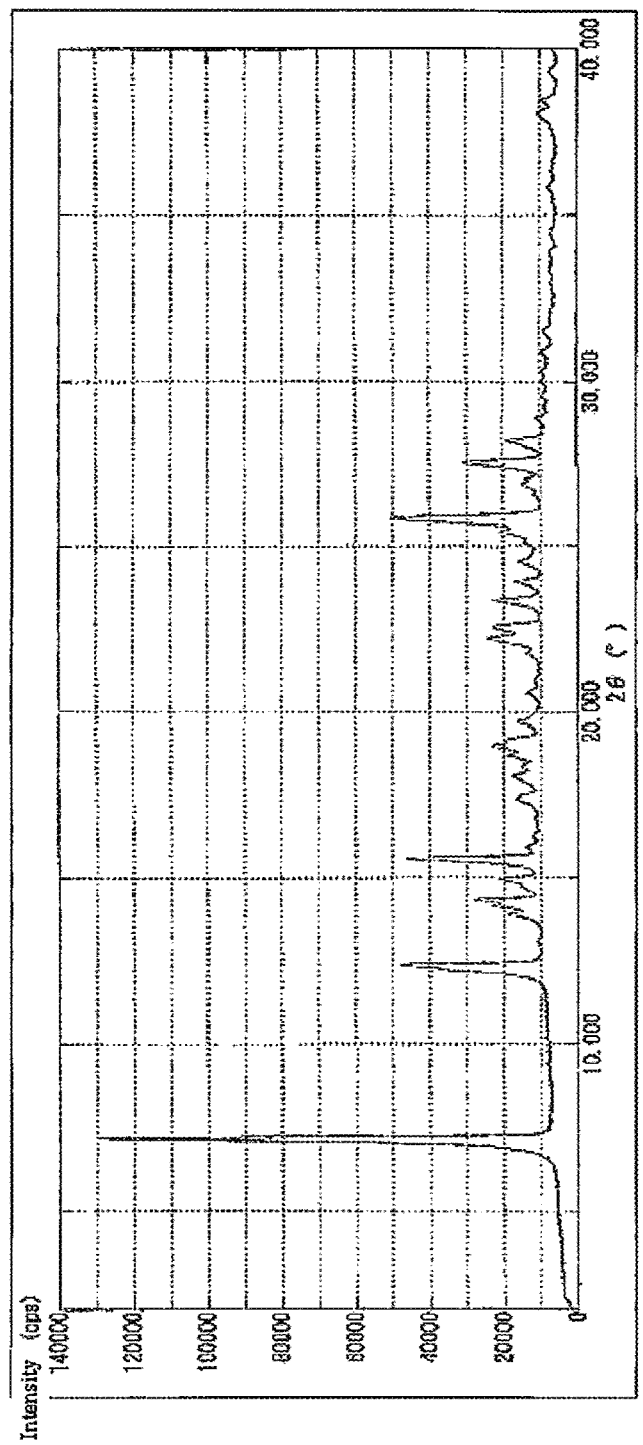
FIG. 4 illustrates powder X-ray diffraction spectrum of monofumarate of Compound A (crystal) synthesized in Example 3 (the axis of ordinates represents intensity (cps), and the axis of abscissas represents diffraction angle (2θ±0.1)).
Figure 5:
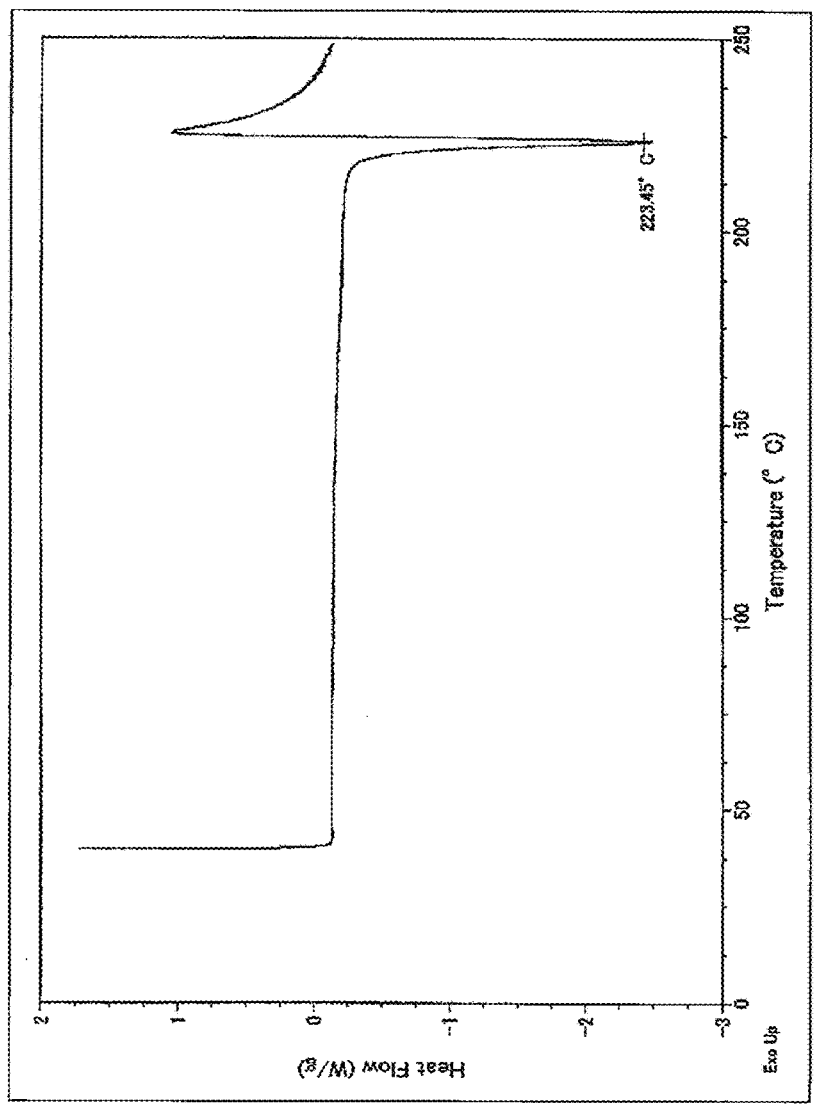
FIG. 5 illustrates a differential scanning calorie (DSC) curve of monofumarate of Compound A (crystal) synthesized in Example 3.
Figure 6:
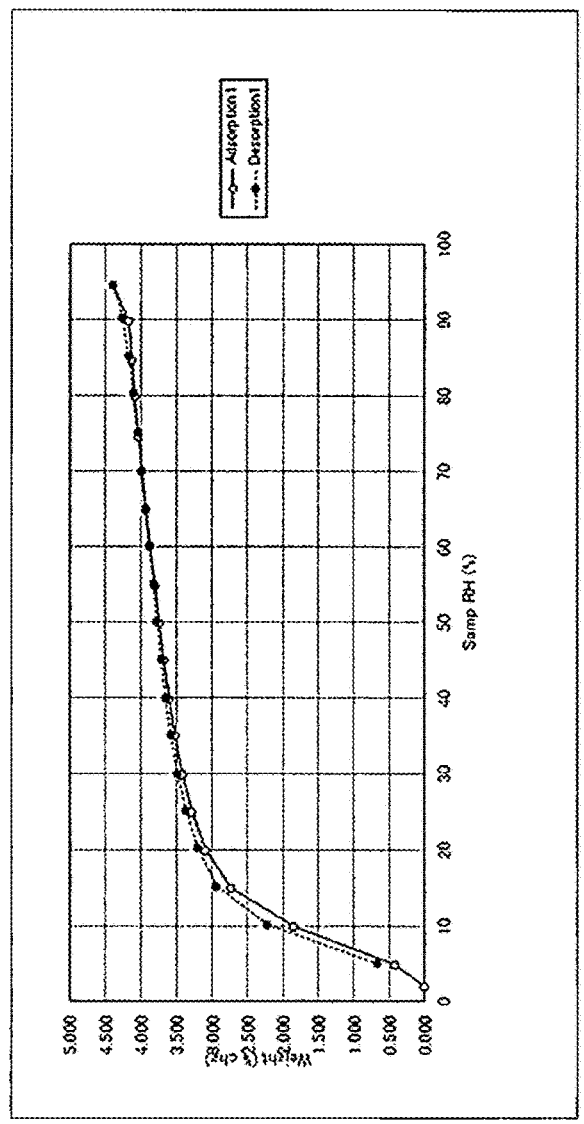
FIG. 6 illustrates a moisture absorption/desorption isothermal curve of Compound A.
Figure 7:
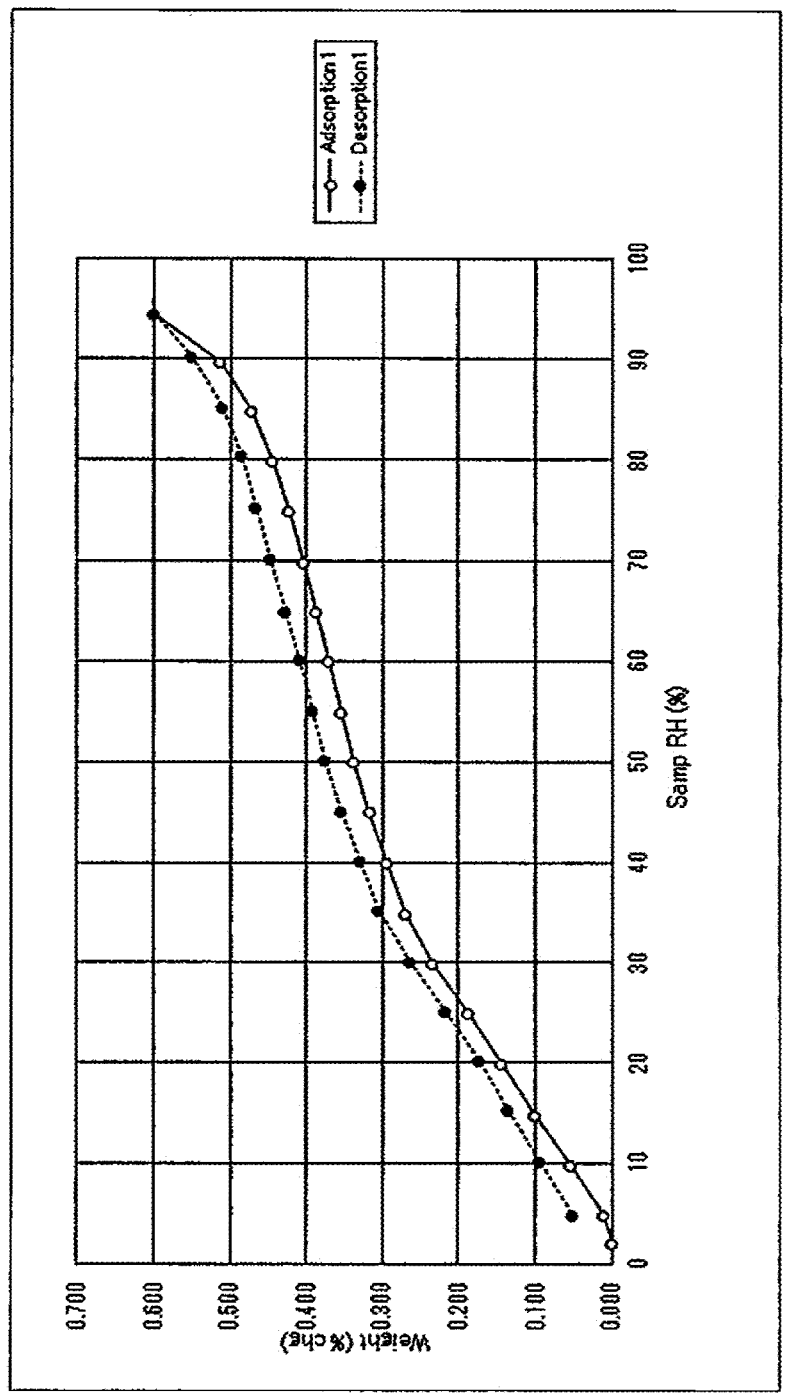
FIG. 7 illustrates a moisture absorption/desorption isothermal curve of monofumarate of Compound A (crystal).
Figure 8:
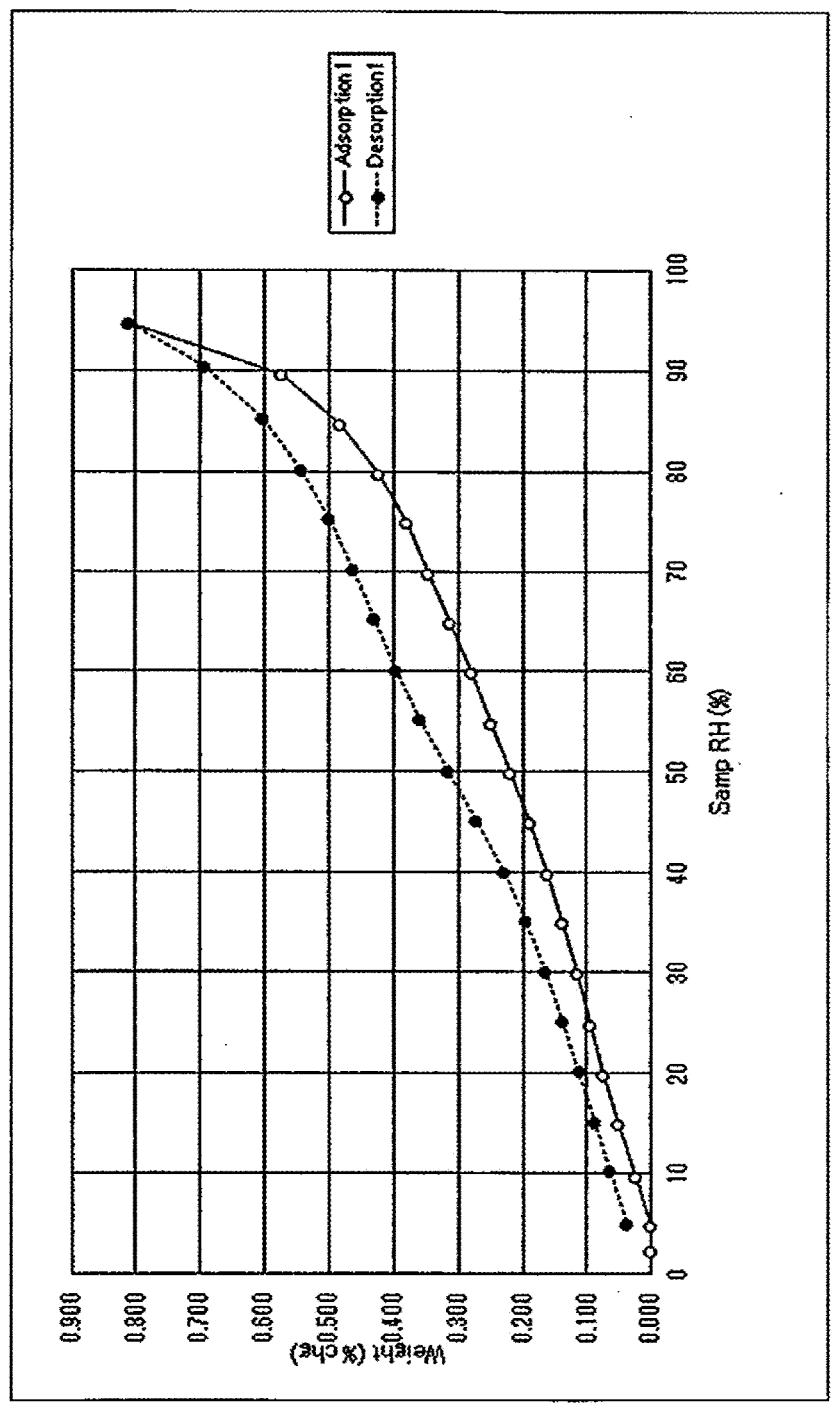
FIG. 8 illustrates a moisture absorption/desorption isothermal curve of hemifumarate of Compound A (crystal).
Figure 9:
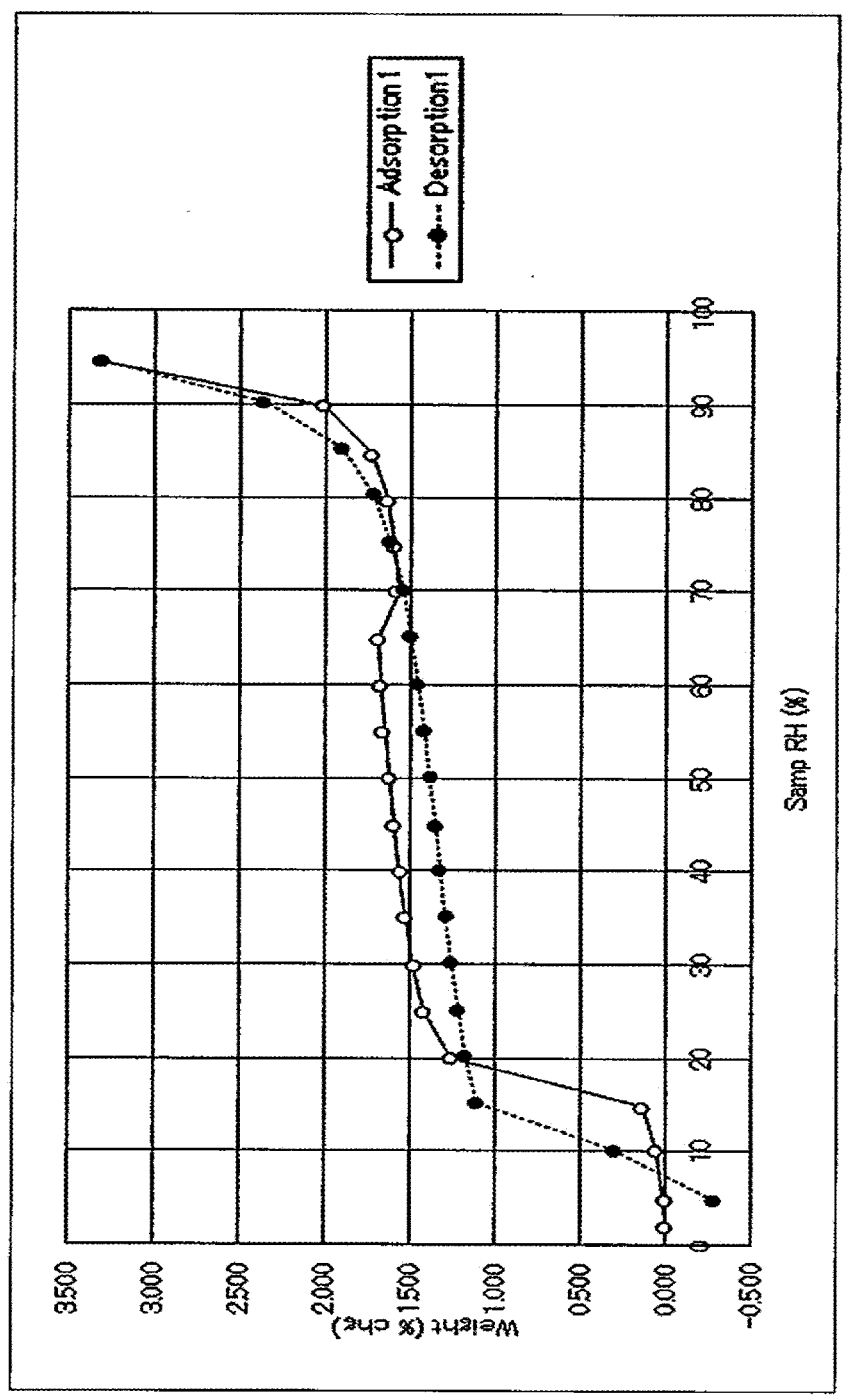
FIG. 9 illustrates a moisture absorption/desorption isothermal curve of hemitartrate of Compound A.
Figure 10:
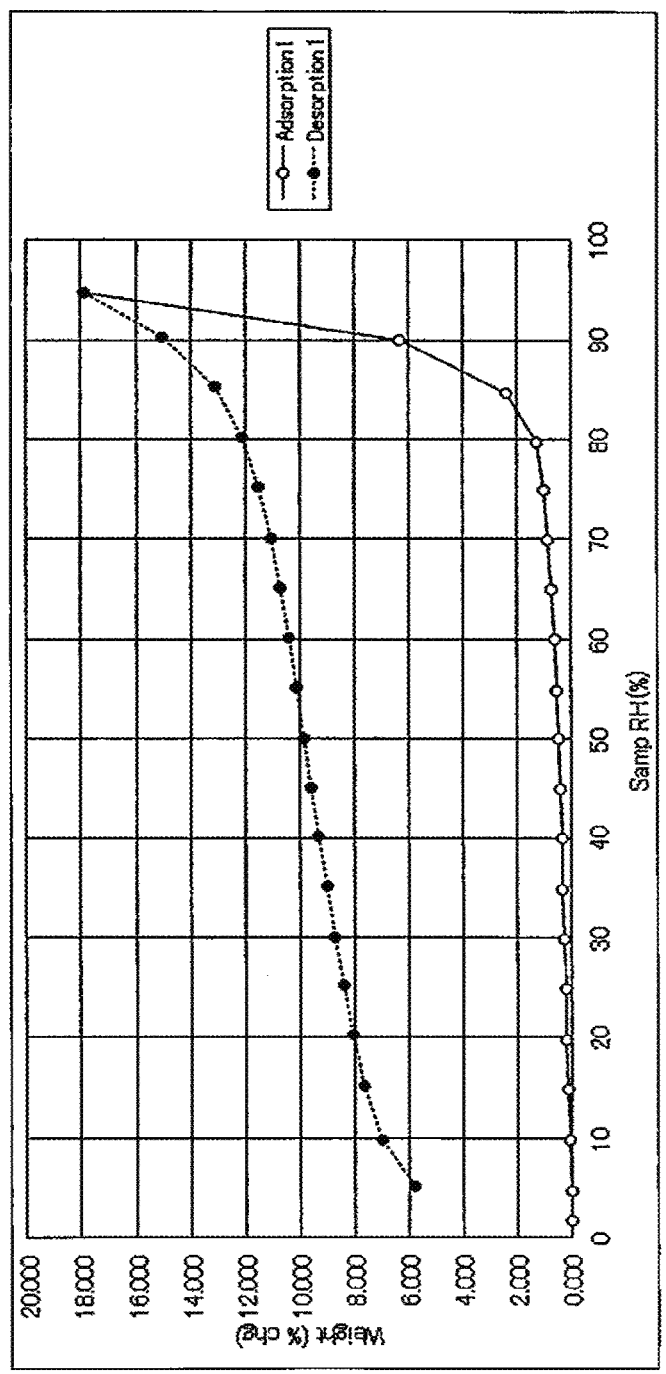
FIG. 10 illustrates a moisture absorption/desorption isothermal curve of monophosphate of Compound A.

It is preferred that the monofumarate of Compound A (crystal) have the powder X-ray diffraction spectrum as shown in FIG. 4 and/or a differential scanning calorie (DSC) curve as shown in FIG. 5.

Here, characteristic peaks of the monofumarate of Compound A (crystal) in a powder X-ray diffraction spectrum may include 7.2°, 12.4°, 15.6°, 25.9° and 27.6°, more preferably 7.2°, 12.4°, 14.4°, 15.0°, 15.6°, 19.0°, 22.3°, 22.6°, 23.4°, 25.5°, 25.9° and 27.6°, in terms of the diffraction angle (2θ±0.1°).

The monofumarate of Compound A (crystal) of the present invention is a crystal having at least two or more peaks selected from the more preferred peaks described above, preferably a crystal having at least three or more peaks selected from the peaks, more preferably a crystal having at least five or more peaks selected from the peaks, even more preferably a crystal having at least eight or more peaks selected from the peaks, and particularly preferably a crystal having all of the peaks described above.

The endothermic peak in a differential scanning calorie (DSC) curve of the monofumarate of Compound A (crystal) may include those in the vicinity of from 219° C. to 224° C., and preferably in the vicinity of 223° C.

Another preferred mode of the monofumarate of Compound A (crystal) of the present invention may be a crystal in which a diffraction angle (2θ±0.1°) has at least two or more, preferably at least three or more, and more preferably at least five or more peaks selected from 7.2°, 12.4°, 15.6°, 25.9° and 27.6° in a powder X-ray diffraction spectrum; and a peak temperature in a differential scanning calorie (DSC) curve has an endothermic peak in the vicinity of from 219 to 224° C., and preferably in the vicinity of 223° C. Even another preferred mode may be a crystal in which a diffraction angle (2θ±0.1°) in a powder X-ray diffraction spectrum has at least two or more, preferably at least three or more, more preferably at least five or more, even more preferably at least eight or more, and still more preferably all of the peaks selected from 7.2°, 12.4°, 14.4°, 15.0°, 15.6°, 19.0°, 22.3°, 22.6°, 23.4°, 25.5°, 25.9° and 27.6°; and at the same time, a peak temperature in a differential scanning calorie (DSC) curve has a endothermic peak in the vicinity of from 219° C. to 224° C., and preferably in the vicinity of 223° C.

Figure 2:
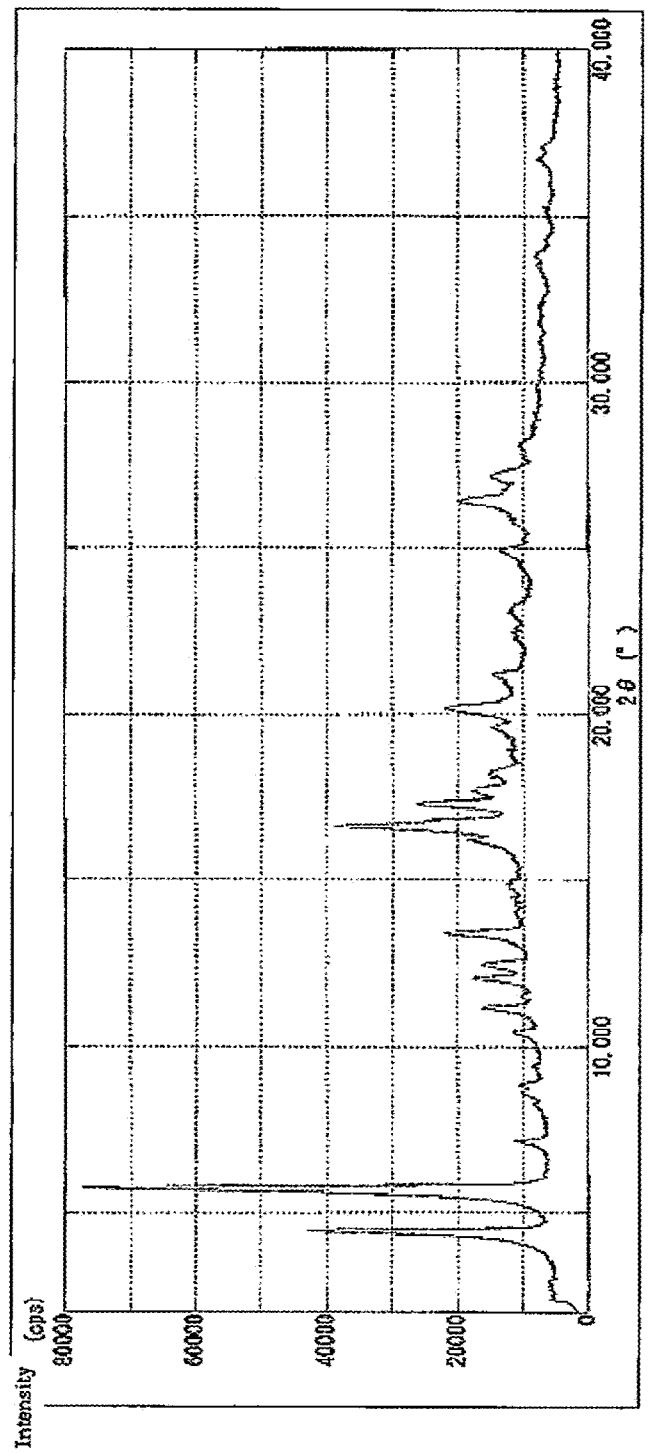
FIG. 2 illustrates powder X-ray diffraction spectrum of hemifumarate of Compound A (crystal) synthesized in Example 2 (the axis of ordinates represents intensity (cps), and the axis of abscissas represents diffraction angle (2θ±0.1°)).
Figure 3:
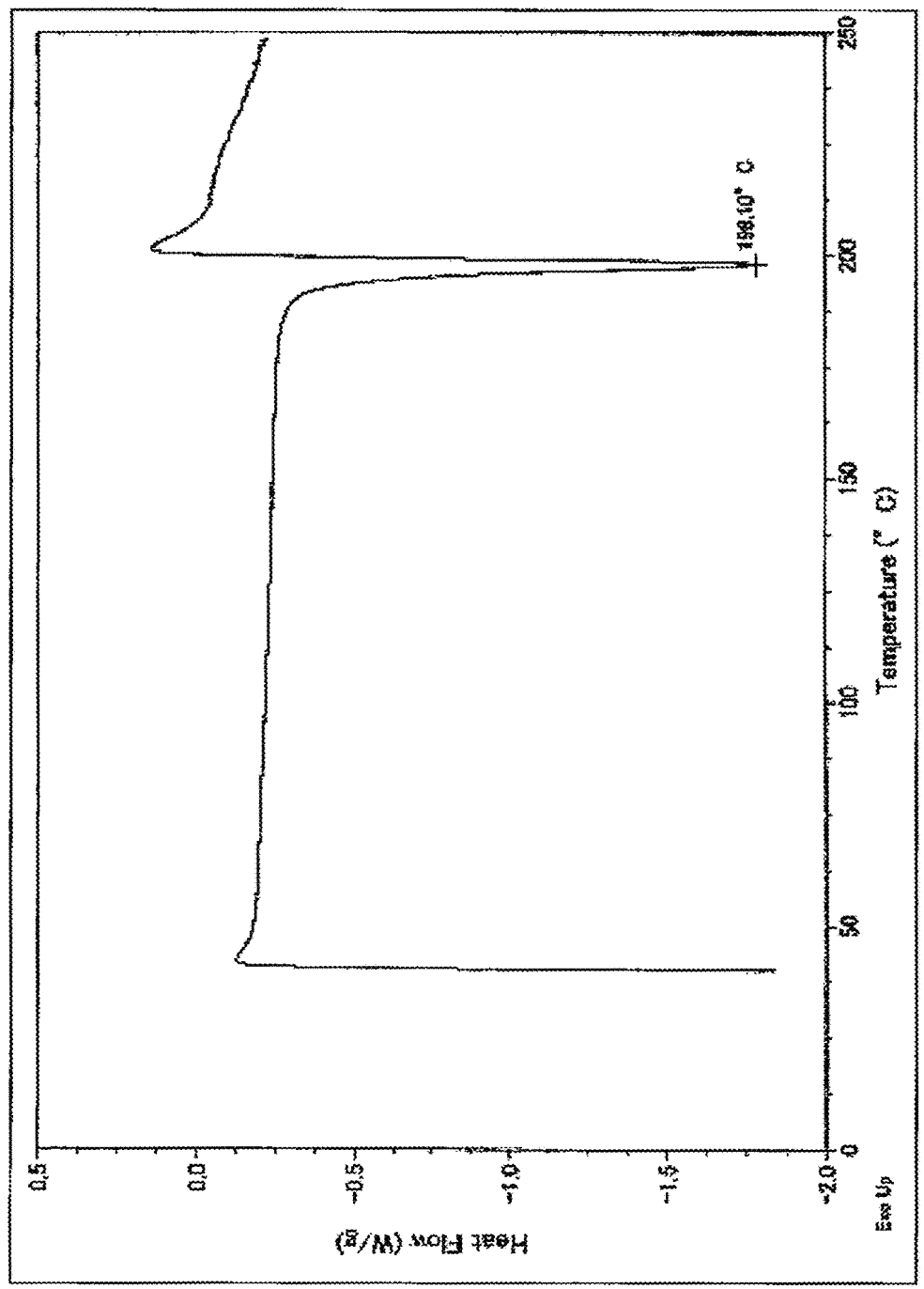
FIG. 3 illustrates a differential scanning calorie (DSC) curve of hemifumarate of Compound A (crystal) synthesized in Example 2.

It is preferred that the hemifumarate of Compound A (crystal) have the powder X-ray diffraction spectrum as shown in FIG. 2 and/or a differential scanning calorie (DSC) curve as shown in FIG. 3.

Here, characteristic peaks of the hemifumarate of Compound A (crystal) in a powder X-ray diffraction spectrum may include 4.5°, 5.8°, 16.6°, 20.2° and 26.4°, and more preferably 4.5°, 5.8°, 11.2°, 12.1°, 12.4°, 13.4°, 16.6°, 17.3°, 18.2°, 20.2°, 26.4° and 27.1°, in terms of the diffraction angle (2θ±0.1°).

The hemifumarate of Compound A (crystal) of the present invention is a crystal having at least two or more peaks selected from the more preferred peaks described above, preferably a crystal having at least three or more peaks selected from the peaks, more preferably a crystal having at least five or more peaks selected from the peaks, even more preferably a crystal having at least eight or more peaks selected from the peaks, and particularly preferably a crystal having all of the peaks.

The endothermic peak in a differential scanning calorie (DSC) curve of the hemifumarate (crystal) of Compound A may include those in the vicinity of from 197° C. to 199° C., and preferably in the vicinity of 198° C.

Other preferred modes of the hemifumarate of Compound A (crystal) of the present invention may include a crystal in which a diffraction angle (2θ±0.1°) has at least two or more, preferably at least three or more, and more preferably at least five or more peaks selected from 4.5°, 5.8°, 16.6°, 20.2° and 26.4° in a powder X-ray diffraction spectrum; and a peak temperature in a differential scanning calorie (DSC) curve has an endothermic peak in the vicinity of from 197 to 199° C., and preferably in the vicinity of 198° C. Still other modes thereof may include a crystal in which a diffraction angle (2θ±0.1°) in a powder X-ray diffraction spectrum has at least two or more, preferably at least three or more, more preferably at least five or more, even more preferably at least eight or more, and still more preferably all of the peaks selected from 4.5°, 5.8°, 11.2°, 12.1°, 12.4°, 13.4°, 16.6°, 17.3°, 18.2°, 20.2°, 26.4° and 27.1°; and at the same time, a peak temperature in the differential scanning calorie (DSC) curve has an endothermic peak in the vicinity of from 197° C. to 199° C., and preferably in the vicinity of 198° C.

Figure 1:
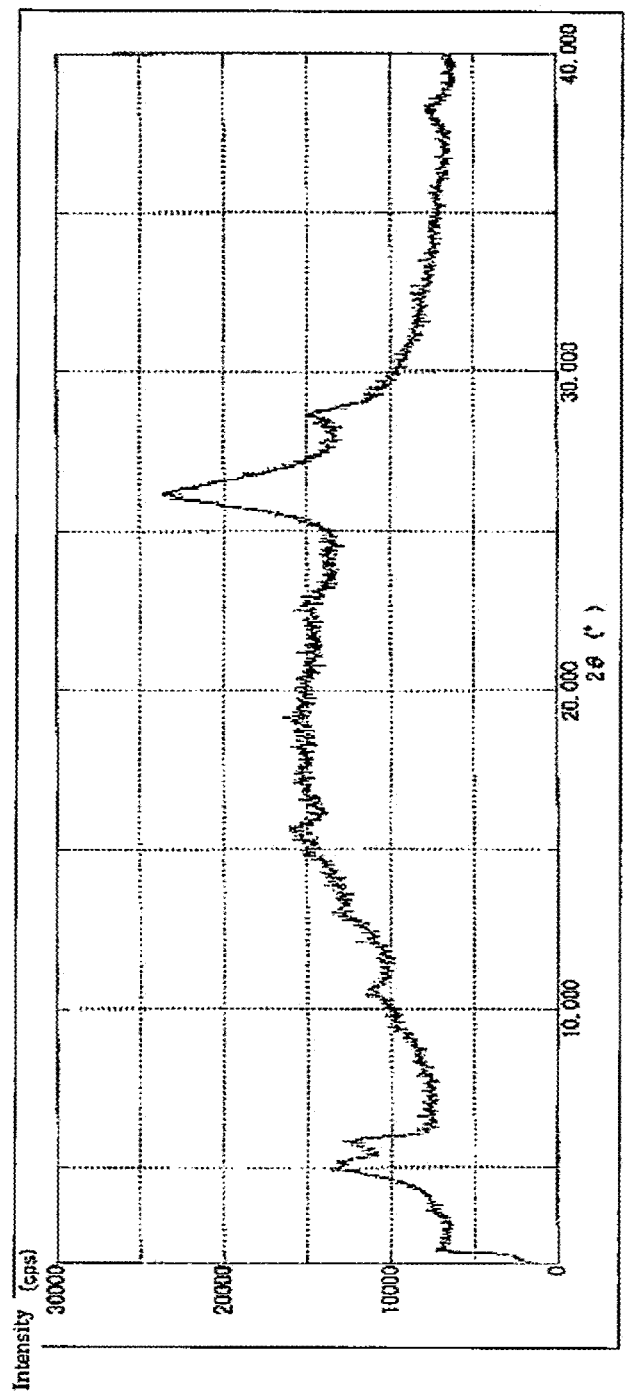
FIG. 1 illustrates powder X-ray diffraction spectrum of monofumarate of Compound A (amorphous) synthesized in Example 1 (the axis of ordinates represents intensity (cps), and the axis of abscissas represents diffraction angle (2θ±0.1°)).

It is also possible to obtain the fumarate of Compound A of the present invention as an amorphous. Specifically, an amorphous of the fumarate of Compound A of the present invention has a diffraction image exhibiting a halo pattern which is broad and unclear in a powder X-ray diffraction spectrum, and more preferably has the powder X-ray diffraction spectrum as shown in FIG. 1.

Compound A can be synthesized, for example, according to the Reference Examples 1 and 2 which will be described later. The synthesis method of Compound A is not limited to the Reference Examples 1 and 2 which will be described later.

More specifically, methanesulfonyl chloride is reacted with (S)—N-Boc-3-pyperidinol in the presence of a tertiary amine such as triethylamine, to obtain (S)-tert butyl 3-(methylsulfonyloxy)piperidine-1-carboxylate. Subsequently, this compound is reacted with 3-iodo-1H-pyrazolo[3,4-d]pyrimidine-4-amine in the presence of a base such as potassium carbonate, to obtain (R)-tert-butyl 3-(4-amino-3-iodo-1H-pyrazolo[3,4-d]pyrimidin-1-yl)piperidine-1-carboxylate. Then, this compound is reacted with a palladium catalyst and a base in the presence of benzo[d]oxazol-2-amine, under a carbon monoxide atmosphere, to obtain (R)-tert-butyl 3-(4-amino-3-((benzo[d]oxazol-2-yl)carbamoyl)-1H-pyrazolo[3,4-d]pyrimidine-1-yl)piperidine-1-carboxylate. Subsequently, a Boc protective group is removed from this compound which is then reacted with acryloyl chloride, to thereby obtain Compound A.

The monofumarate of Compound A of the present invention (amorphous) may be produced, for example, in the following method.

To the Compound A is added tetrahydrofuran (THF) in an amount of from 100 to 300 times, and preferably 150 times thereof, and water in an amount of from 0.01 to 1 times, preferably 0.1 times thereof. To the mixture, fumaric acid in a molar amount equal to Compound A is added and dissolved.

The solvent is distilled off with azeotropically distilling the mixture with THF several times, preferably 2 times to 5 times. Thus, it is possible to obtain an amorphous of monofumarate of Compound A as a white powder.

The monofumarate of Compound A (crystal) of the present invention may be obtained as a white powder, for example, by suspending monofumarate of Compound A (amorphous) in acetonitrile in an amount of from 5 to 50 times, preferably 20 times thereof, and conducting a heating suspension for from 12 to 72 hours, preferably for 24 hours.

The hemifumarate of Compound A (crystal) of the present invention may be obtained as a white powder, for example, by suspending monofumarate of Compound A (amorphous) in methyl ethyl ketone in an amount of from 10 to 100 times, preferably 60 times thereof, and conducting a heating suspension for from 12 to 72 hours, preferably for 24 hours.

According to the fumarate of Compound A of the present invention, it is possible to avoid the characteristic of channel hydrate of Compound A.

Generally, in a pharmaceutical product or a drug ingredient for a pharmaceutical product which is prepared with a compound with the characteristic of channel hydrate avoided, it is known that problems in storage and in quality control in a humidity of a storage condition thereof are reduced; and also that, when a solid preparation such as a tablet or a capsule is produced, it is possible to reduce problems in preparation due to a weight change of an active ingredient.

Therefore, it can be said that, according to the fumarate of Compound A of the present invention, it is possible to expect a stable storage and easy quality control, and also that, in terms of preparation, the fumarate of Compound A of the present invention is an excellent compound which is easy to handle.

The fumarate of Compound A of the present invention is excellent in obtaining-operability and in reproducibility, compared to other salts of Compound A. Specifically, for example, a salt of Compound A with hydrochloric acid, sulfuric acid, succinic acid, malic acid, citric acid, or acetic acid was not formed by the research method described in the present specification. For example, in a formation of sodium salt of Compound A, decomposition remarkably proceeded. When a hemi magnesium salt of Compound A was synthesized, the number of analogous substances was increased, and moreover, operation of obtaining the salt was complex, and the salt was hard to redissolve, for its a low solubility to water and to an organic solvent.

The fumarate of Compound A of the present invention is easy to handle as a drug ingredient for a pharmaceutical product, and contributes to industrial production of pharmaceutical product having a stable quality.

The fumarate of Compound A of the present invention is excellent in solid stability. It is important for a candidate compound to be developed as a pharmaceutical product to have a solid stability, in an industrial operation and in maintaining a quality. Therefore, the fumarate of Compound A of the present invention has excellent properties required for a pharmaceutical product or a drug ingredient for a pharmaceutical product.

The fumarate of Compound A of the present invention is excellent in oral absorption property, and contributes in providing an excellent pharmaceutical product with a high quality.

Among the salts of Compound A, fumarate of Compound A of the present invention is excellent in any of obtaining-operability, reproducibility, solid stability, and oral absorption property, while avoiding the characteristic of channel hydrate that Compound A has and maintaining a sufficient solubility as a drug ingredient for a pharmaceutical product.

The fumarate of Compound A of the present invention has an excellent BTK inhibitory activity, and is useful as a preventive and/or therapeutic agent of, for example, cancers, tumors, and various immune diseases (for example, allergic diseases, autoimmune diseases, and inflammatory diseases). Furthermore, the fumarate has an excellent selectivity to BTK, and has an advantage of having reduced adverse effects derived from inhibiting other kinases (for example, EGFR) as well.

The fumarate of Compound A of the present invention has excellent BTK inhibitory activity. "BTK" according to the present specification includes human or non-human mammalian BTK's, and the BTK is preferably human BTK. Incidentally, the term "BTK" includes its isoforms.

Furthermore, due to its excellent BTK inhibitory activity, the fumarate of Compound A of the present invention is useful as a medicine for the prevention or treatment of diseases associated with BTK. The "diseases associated with BTK" include diseases that undergo a decrease in the incidence rate and remission, alleviation and/or complete recovery of symptoms, as a result of deletion, suppression and/or inhibition of the functions of BTK. Examples of such diseases include cancers or tumors, allergic diseases, autoimmune diseases, inflammatory diseases, graft-versus-host disease without limitation, and are preferably cancers, tumors, allergic diseases and autoimmune diseases.

There is no particular limitation on the target cancers and tumors, and examples thereof include epithelial cancers (for example, respiratory system cancers, gastrointestinal system cancers, reproductive system cancers, and secretion system cancers), sarcomas, hematopoietic system tumors, central nervous system tumors, and peripheral nerve tumors. Preferred examples are hematopoietic system tumors (for example, leukemia, multiple myeloma, and malignant lymphoma). Furthermore, there is no particular limitation on the kind of the organs of tumor development, and examples thereof include head and neck carcinoma, esophageal cancer, stomach cancer, colon cancer, rectal cancer, liver cancer, gall bladder/bile duct cancer, biliary tract cancer, pancreatic cancer, lung cancer, breast cancer, ovarian cancer, cervical cancer, uterine cancer, kidney cancer, urinary bladder cancer, prostate cancer, testicular tumors, bone/soft tissue sarcoma, hematologic tumors, multiple myeloma, skin cancer, brain tumors, and mesothelial cancer. Preferred examples of the hematopoietic system tumors include acute leukemia, acute promyelocytic leukemia, acute lymphoblastic leukemia, chronic myelogenous leukemia, lymphoblastic lymphoma, myeloproliferative neoplasms, chronic lymphocytic leukemia, small lymphocytic lymphoma, myelodysplastic syndromes, follicular lymphoma, MALT lymphoma, marginal zone lymphoma, lymphoplasmacytic lymphoma, Waldenstroem macroglobulinemia, mantle cell lymphoma, diffuse large B-cell lymphoma, Burkitt's lymphoma, extranodal NK/T-cell lymphoma, Hodgkin's lymphoma, and multiple myeloma. Particularly preferred examples include hematologic tumors such as B-lymphoblastic leukemia/lymphoma, follicular lymphoma, mantle cell lymphoma, nodal follicular marginal zone lymphoma, diffuse large B-cell lymphoma, Burkitt's lymphoma, chronic lymphocytic leukemia, small lymphocytic lymphoma, Waldenstroem macroglobulinemia, extranodal NK/T-cell lymphoma, Hodgkin's lymphoma, myelodysplastic syndromes, acute myelogenous leukemia, and acute lymphocytic leukemia.

There is no particular limitation on the target allergic diseases, and examples thereof include, for example, bronchial asthma, allergic rhinitis, pollinosis, atopic dermatitis, food allergy, anaphylaxis, drug allergy, hives, and conjunctivitis. Preferred examples thereof include bronchial asthma, allergic rhinitis, pollinosis, and atopic dermatitis; and particularly preferred examples thereof include allergic rhinitis, pollinosis and atopic dermatitis.

There is no particular limitation on the target autoimmune diseases, and examples thereof include rheumatoid arthritis, systemic lupus erythematosus, dermatosclerosis, polymyositis, Sjögren's syndrome, and Behcet's disease. Preferred examples thereof include rheumatoid arthritis and systemic lupus erythematosus, and particularly preferred example is rheumatoid arthritis.

There is no particular limitation on the target inflammatory diseases, and examples thereof include appendicitis, blepharitis, bronchiolitis, bronchitis, bursitis, cervicitis, cholangitis, cholecystitis, ulcerative colitis, Crohn's disease, irritable bowel syndrome, cystitis, dacryoadenitis, contact dermatitis, dermatomyositis, cerebritis, endocarditis, endometritis, epididymitis, fasciitis, fibrositis, gastroenteritis, hepatitis, sudoriferous abscess, laryngitis, mastitis, meningitis, myelitis, myocarditis, nephritis, ovaritis, didymitis, pancreatitis, parotitis, pericarditis, peritonitis, pharyngitis, pleuritis, phlebitis, pneumonia, rectitis, prostatitis, pyelonephritis, salpingitis, nasosinusitis, stomatitis, osteoarthritis, synovitis, tendinitis, tonsillitis, uveitis, vaginitis, vasculitis, and vulvitis. Preferred examples may include ulcerative colitis, Crohn's disease, irritable bowel syndrome, contact dermatitis, cystitis, and osteoarthritis. Particularly preferred examples may include contact dermatitis, cystitis, and osteoarthritis.

When the fumarate of Compound A of the present invention is used as a pharmaceutical composition, various dosage forms can be employed according to the purpose of prevention or treatment by incorporating pharmaceutical carriers as necessary. The dosage form may be, for example, any of an oral preparation, an injectable preparation, a suppository preparation, an ointment, and a patch. Any of these dosage forms can be produced by a formulation method that is publicly known and conventionally used by those skilled in the art. Particularly, a tablet for oral administration, a coated tablet, a pill, a granular preparation, a powder preparation, and a capsule preparation which contain a crystal of the fumarate of Compound A as a drug ingredient for production are advantageous as a stable solid preparation.

Regarding the pharmaceutical carriers, various organic or inorganic carrier materials that are conventionally used as formulation materials are used, and the pharmaceutical carriers are incorporated as, for example, an excipient, a binder, a disintegrant, a lubricant, and a coating agent in solid preparations; and as a solvent, a dissolution aid, a suspending agent, an isotonic agent, a pH adjusting agent, a buffering agent, and an analgesic agent in liquid preparations. Furthermore, if necessary, formulation additives such as an antiseptic, an antioxidant, a colorant, a flavoring/savoring agent, and a stabilizer can also be used.

Examples of the excipient include lactose, sucrose, D-mannitol, starch, crystalline cellulose, and calcium silicate.

Examples of the binder include hydroxypropyl cellulose, methyl cellulose, polyvinylpyrrolidone, sugar powder, and hypromellose.

Examples of the disintegrant include sodium starch glycolate, carmellose calcium, croscarmellose sodium, crospovidone, low-substituted hydroxypropyl cellulose, and partially gelatinized starch.

Examples of the lubricant include talc, magnesium stearate, sucrose fatty acid esters, stearic acid, and sodium stearyl fumarate.

Examples of the coating agent include ethyl cellulose, aminoalkyl methacrylate copolymer RS, hypromellose, and sucrose.

Examples of the solvent include water, propylene glycol, and physiological saline.

Examples of the dissolution aid include polyethylene glycol, ethanol, α-cyclodextrin, Macrogol 400, and Polysorbate 80.

Examples of the suspending agent include carrageenan, crystalline cellulose, carmellose sodium, and polyoxyethylene hydrogenated castor oil.

Examples of the isotonic agent include sodium chloride, glycerin, and potassium chloride.

Examples of the pH adjusting agent and the buffering agent include sodium citrate, hydrochloric acid, lactic acid, phosphoric acid, and sodium dihydrogen phosphate.

Examples of the analgesic agent include procaine hydrochloride and lidocaine.

Examples of the antiseptic agent include ethyl paraoxybenzoate, cresol, and benzalkonium chloride.

Examples of the antioxidant include sodium sulfite, ascorbic acid, and natural vitamin E.

Examples of the colorant include titanium oxide, iron sesquioxide, Edible Blue No. 1, and copper chlorophyll.

Examples of the flavoring/savoring agent include aspartame, saccharin, sucralose, 1-menthol, and mint flavor.

Examples of the stabilizer include sodium pyrosulfite, sodium edetate, erythorbic acid, magnesium oxide, and dibutylhydroxytoluene.

In preparing an oral solid preparation, an excipient, a binder, a disintegrant, a lubricant, a colorant, and a flavoring/savoring agent are optionally added to the fumarate of Compound A, and then, for example, a tablet, a coated tablet, a granular preparation, a powder preparation, or a capsule preparation can be produced by a conventional method.

In preparing an injectable preparation, a pH adjusting agent, a buffering agent, a stabilizer, an isotonic agent, and a local anesthetic are added to the fumarate of Compound A, and subcutaneous, intramuscular, and intravenous injectable preparations can be produced by conventional methods.

The amounts of the fumarate of Compound A to be incorporated into the various unit dosage forms may vary depending on the symptoms of the patient to whom this fumarate should be applied, or depending on the formulation form; however, it is generally desirable to adjust the amount to from 0.05 to 1,000 mg in an oral preparation, to from 0.01 to 500 mg in an injectable preparation, and to from 1 to 1,000 mg in a suppository preparation, per unit dosage form.

Furthermore, the daily dose of a medicament having the dosage form described above may vary with, for example, the symptoms, body weight, age and gender of the patient, and cannot be determined indiscriminately. However, the dose may usually be adjusted to from 0.05 to 5,000 mg, and preferably from 0.1 to 1,000 mg, per day for an adult (body weight: 50 kg), and it is preferable to administer this amount once a day, or in divided portions in about two to three times a day.

EXAMPLES

Hereinafter, the present invention will be described more specifically by way of Examples, but the present invention is not intended to be limited to these. Although the present invention is sufficiently described by the Examples, it should be understood that various changes or modifications can be done by those skilled in the art. Therefore, such changes or modifications are involved in the present invention, unless they deviate from the scope of the present invention.

Regarding the various reagents used in the Examples, unless particularly stated otherwise, commercially available products were used. For silica gel column chromatography, a PURIF-PACK (registered trademark) SI manufactured by Schott Moritex Corp., a KP-Sil (registered trademark) Silica Prepacked Column manufactured by Biotage AB, or an HP-Sil (registered trademark) Silica Prepacked Column manufactured by Biotage AB was used. For basic silica gel column chromatography, a PURIF-PACK (registered trademark) NH manufactured by Moritex Corp., or a KP-NH (registered trademark) Prepacked Column manufactured by Biotage AB was used. For thin layer chromatography for fractionation, a KIESELGEL TM60F254, Art. 5744 manufactured by Merck KGaA, or a NH2 silica gel 60F254 plate manufactured by Wako Pure Chemical Industries, Ltd. was used. The NMR spectrum was measured with an AL400 (400 MHz; JEOL, Ltd.), a MERCURY400 (400 MHz; Agilent Technologies, Inc.) type spectrometer, or an INOVA400 (400 MHz; Agilent Technologies, Inc.) equipped with an 400MNMR probe (Protasis Corp.) type spectrometer, and with tetramethylsilane as the internal reference in a case in which the deuterated solvent contains tetramethylsilane, while in other cases, with an NMR solvent as the internal reference. All the δ values were expressed in ppm.

The LCMS spectrum was measured with an ACQUITY SQD (quadrupole type) manufactured by Waters Corp. under the conditions described below.

Column: YMC-TRIART C18 manufactured by YMC Co., Ltd., 2.0×50 mm, 1.9 μm
  MS detection: ESI positive
  UV detection: 254 nm and 210 nm
  Column flow rate: 0.5 mL/min
  Mobile phase: Water/acetonitrile (0.1% formic acid)
  Amount of injection: 1 μL
  Gradient (Table 1)

TABLE 1

| Time (min) | Water | Acetonitrile |
|---|---|---|
| 0-0.1 | 95% | 5% |
| 0.1-2.1 | 95% to 5% | 5% to 95% |
| 2.1-3.1 | 5% | 95% |

Furthermore, reverse phase preparative HPLC purification was carried out with a preparative system manufactured by Waters Corp. under the conditions described below.

Column: YMC-ACTUS TRIART C18 manufactured by YMC Co., Ltd., 20×50 mm, 5 μm, connected with YMC-ACTUS TRIART C18 manufactured by YMC Co., Ltd. 20×10 mm, 5 μm, was used.
  UV detection: 254 nm
  MS detection: ESI positive
  Column flow rate: 25 mL/min
  Mobile phase: Water/acetonitrile (0.1% formic acid)
  Amount of injection: 0.1 to 0.5 mL
  The meanings of abbreviations are shown below.
  s: Singlet
  d: Doublet
  t: Triplet
  q: Quartet
  dd: Double doublet
  dt: Double triplet
  td: Triple doublet
  tt: Triple triplet
  ddd: Double doublet
  ddt: Double triplet
  dtd: Double triple doublet
  tdd: Triplet double doublet
  m: Multiplet
  br: Broad
  brs: Broad singlet
  CDI: Carbonyldiimidazole
  DMSO-$d_6$: Deuterated dimethyl sulfoxide
  $CDCl_3$: Deuterated chloroform
  $CD_3OD$: Deuterated methanol
  THF: Tetrahydrofuran
  DMF: N,N-dimethylformamide
  DMA: N,N-dimethylacetamide
  NMP: 1-Methyl-2-pyrrolidinone
  DMSO: Dimethyl sulfoxide
  TFA: Trifluoroacetic acid
  WSC: 1-(3-Dimethylaminopropyl)-3-ethylcarbodiimide hydrochloride
  HOBt: 1-Hydroxybenzotriazole monohydrate
  HATU: (Dimethylamino)-N,N-dimethyl(3H-[1,2,3]triazolo[4,5-b]pyridin-3-yloxy)methaneiminium hexafluorophosphate
  DIAD: Diisopropyl azodicarboxylate
  TBAF: Tetrabutylammonium fluoride
  DIPEA: Diisopropylethylamine
  Boc: Tert-butoxycarbonyl
  $Boc_2O$: Di-tert-butyl dicarbonate
  DMAP: Dimethylaminopyridine
  Powder X-Ray Diffraction Measurement The powder X-ray diffraction was measured in accordance with the following test conditions, after a test substance is lightly pulverized as needed in an agate mortar.

Device: Rigaku MiniFlexII
Target: Cu
X-ray output setting: 15 mA, 30 kV
Scanning area: 2.0 to 40.0°
Step size: 0.010°
Scanning speed: 5.00°/min.
Divergence Slit: 1.25°
Scattering Slit: Open
Light receiving slit: Open Handling of the devices including data processing was based on the method and the process indicated in each device.

Numerical values obtained from various spectrums may slightly fluctuate according to direction of crystal growth, size of particles, or condition of measurement thereof. Therefore, those numerical values should not be strictly interpreted.

Thermal Analysis Measurement (Differential Scanning Calorie Measurement (DSC Measurement))

DSC measurement was measured in accordance with the following test conditions.

Device: TA Instrument Q1000
Sample: About 1 mg
Sample container: Aluminum made
Temperature rising speed: Raised by 5° C./min., up to 250° C.
Atmospheric gas: Nitrogen
Flow rate of nitrogen gas: 50 mL/min.

Handling of the devices including data processing was based on the method and the process indicated in each device.

Reference Example 1

Synthesis of (R)-tert-butyl 3-(4-amino-3-iodo-1H-pyrazolo[3,4-d]pyrimidin-1-yl)piperidine-1-carboxylate

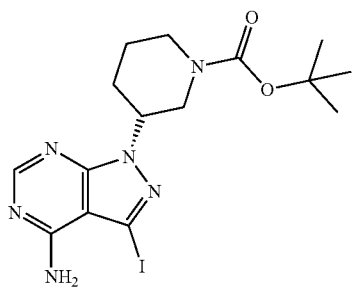

(Step 1) Synthesis of (S)-tert-butyl 3-(methylsulfonyloxy)piperidine-1-carboxylate 20 g of (S)—N-Boc-3-piperidinol was dissolved in 100 mL of toluene, and 21 mL of triethylamine and 9.2 mL of methanesulfonyl chloride were added thereto at 0° C. The mixture was stirred for 1 hour under ice cooling, subsequently ethyl acetate and water were added thereto, and an organic layer was separated. The organic layer was washed with a saturated aqueous solution of sodium hydrogen carbonate, a saturated aqueous solution of ammonium chloride and water, and then was dried over anhydrous sodium sulfate. The solvent was distilled off under reduced pressure, and thus 26.8 g of the title compound was obtained as a colorless solid.

(Step 2) Synthesis of (R)-tert-butyl 3-(4-amino-3-iodo-1H-pyrazolo[3,4-d]pyrimidin-1-yl)piperidine-1-carboxylate A suspension solution of 14.6 g of 3-iodo-1H-pyrazolo[3,4-d]pyrimidin-4-amine synthesized by the method described in WO 2007/126841, 25 g of (S)-tert-butyl 3-(methylsulfonyloxy)piperidine-1-carboxylate obtained in Step 1, and 69 g of potassium carbonate in 150 mL of DMA was heated to 100° C., and was stirred for 10 hours. The suspension solution was cooled to room temperature, and then 300 mL of water was added thereto. A solid thus obtained was collected by filtration and washed with water, and the solid was dried. Thus, 26.9 g of the title compound was obtained as a yellow solid.

Reference Example 2

Synthesis of (R)-1-(1-acryloylpiperidin-3-yl)-4-amino-N-(benzo[d]oxazol-2-yl)-1H-pyrazolo[3,4-d]pyrimidine-3-carboxamide (Compound A)

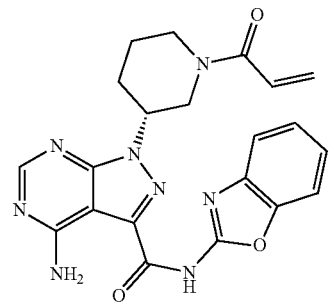 [SMILES: C=CC(=O)N1CCC[C@@H](n2nc(C(=O)Nc3nc4ccccc4o3)c3c(N)ncnc32)C1]

(Step 1) Synthesis of (R)-tert-butyl 3-(4-amino-3-((benzo[d]oxazol-2-yl)carbamoyl)-1H-pyrazolo[3,4-d]pyrimidin-1-yl)piperidine-1-carboxylate 300 mg of (R)-tert-butyl 3-(4-amino-3-iodo-1H-pyrazolo[3,4-d]pyrimidin-1-yl)piperidine-1-carboxylate obtained in Reference Example 1 was dissolved in 3 mL of NMP. 118 mg of benzo[d]oxazol-2-amine, 20 mg of xantphos, and 0.15 mL of N-methylmorpholine were added thereto, and a degassing operation was carried out. Thereafter, 7.6 mg of palladium acetate was added thereto, and under a carbon monoxide atmosphere, the mixture was heated to 110° C. and stirred for 2 hours. After the mixture was cooled, 4.5 mL of methanol and 0.45 mL of a 5 N aqueous solution of sodium hydroxide were added thereto, and the mixture was stirred for 30 minutes at room temperature. Thereafter, the pH was adjusted to 5.3 with 2 N HCl, and a solid thus obtained was collected by filtration. The crude product was purified by a silica gel column (chloroform-methanol), and thus 257 mg of the title compound was obtained as a white solid.

(Step 2) Synthesis of Compound A 5.0 g of (R)-tert-butyl 3-(4-amino-3-((benzo[d]oxazol-2-yl)carbamoyl)-1H-pyrazolo[3,4-d]pyrimidin-1-yl)piperidine-1-carboxylate obtained in Step 1 was suspended in 50 mL of acetonitrile, and to the mixture was added 7.85 g of sodium iodide. 6.65 mL of trimethylsilyl chloride was added dropwise thereto with stirring at room temperature, and the mixture was stirred for 1 hour. 87.5 mL of water and 12.5 mL of a 5 N aqueous solution of sodium hydroxide were added thereto, and then the system was ice-cooled. A solution prepared by dissolving 0.895 mL of acryloyl chloride to 4.1 mL of acetonitrile was added dropwise thereto, and the mixture was stirred for 1 hour under ice cooling. 50 mL of water was added thereto, and a solid thus produced was collected by filtration, washed with water, and dried under a reduced pressure. Thus, 4.13 g of the title compound was obtained as a white solid (Compound A).

$^1$H-NMR (DMSO-$d_6$): δppm 1.53-1.68 (m, 1H), 1.86-1.98 (m, 1H), 2.08-2.21 (m, 1H), 2.25-2.39 (m, 1H), 2.82-2.95 (m, 0.5H), 3.10-3.22 (m, 0.5H), 3.23-3.37 (m, 0.5H), 3.68-3.78 (m, 0.5H), 4.04-4.14 (m, 0.5H), 4.22-4.38 (m, 1H), 4.52-4.65 (m, 0.5H), 4.67-4.81 (m, 1H), 5.58-5.74 (m, 1H), 6.03-6.19 (m, 1H), 6.68-6.92 (m, 1H), 7.28-7.40 (m, 2H), 7.59-7.71 (m, 2H), 8.22 (brs, 2H), 8.28 (s, 1H), 12.15 (brs, 1H)

Reference Example 3

Research of (R)-1-(1-acryloylpiperidin-3-yl)-4-amino-N-(benzo[d]oxazol-2-yl)-1H-pyrazolo[3,4-d]pyrimidine-3-carboxamide (Compound A) and acid or base addition salts (1) Research of Acid Addition Salts of Compound A A research was carried out on salt formation with hydrochloric acid, sulfuric acid and phosphoric acid among inorganic acids. Specifically, Compound A was dissolved in an appropriate solvent, and each kind of the acids in an appropriate amount (from 0.5 to 1.5 equivalent) was added thereto, and stirring was carried out for overnight, to thereby determine whether or not a salt formation occurred. As a result, in adding hydrochloric acid or sulfuric acid to Compound A, decomposition remarkably proceeded, and therefore, the research was suspended. In adding phosphoric acid to Compound A, monophosphate of Compound A was obtained (Reference Example 4).

In addition, research was carried out on salt formation with fumaric acid, succinic acid, tartaric acid, malic acid, citric acid and acetic acid. Specifically, Compound A was dissolved in an appropriate solvent, and each kind of the acids in a molar amount equal to Compound A was added thereto, and thereafter, the solvent was distilled off to thereby prepare an amorphous of each kind of organic acids. Subsequently, this amorphous was suspended with heating in an organic solvent (for example, methylethylketone, ethanol, ethyl acetate and butyl acetate), to thereby determine whether or not a salt formation occurred. As a result, no salt was formed with malic acid, citric acid or acetic acid. From an amorphous of succinic acid, although a crystalline substance was obtained, it was not possible to obtain succinate in an amount equivalent to a theoretical amount. From fumaric acid, monofumarate of Compound A (amorphous) was obtained, and from tartaric acid, hemitartrate of Compound A was obtained (Example 1 and Reference Example 5).

(2) Research of Base Addition Salts of Compound A

A research was carried out on salt formation with sodium and magnesium, among inorganic bases. Specifically, Compound A was dissolved in an appropriate solvent, and each kind of the bases was added thereto (from 0.5 to 1.5 equivalent), and stirring was carried out for overnight, to thereby determine whether or not a salt formation occurred. As a result, in salt formation with sodium, decomposition remarkably proceeded, and therefore, the research was suspended. From the case of magnesium, hemi magnesium salt of Compound A was obtained (Reference Example 6). However, in the hemi magnesium salt of Compound A, the number of analogous substances was increased, and moreover, an operation of obtaining the salt was complex, and redissolution was difficult, for its low solubility to an organic solvent, and therefore, it was judged that the salt was inappropriate for a practical production.

Reference Example 4

Synthesis of (R)-1-(1-acryloylpiperidin-3-yl)-4-amino-N-(benzo[d]oxazol-2-yl)-1H-pyrazolo[3,4-d]pyrimidine-3-carboxamide.monophosphate (monophosphate of Compound A)

To the Compound A obtained above (150 mg) was added THF (18 mL), and after the mixture was heated to 70° C., was added phosphoric acid (27.3 μL) thereto. Thereafter, the mixture was stirred at the same temperature for 72 hours, and a deposited solid was collected by filtration, then dried under a reduced pressure, and the title compound was obtained as a white solid. Amount of yield: 158 mg, Ratio of yield: 85.9%

$^1$H-NMR (DMSO-$d_6$): δppm 1.51-1.69 (m, 1H), 1.87-1.97 (m, 1H), 2.09-2.21 (m, 1H), 2.25-2.41 (m, 1H), 2.84-2.95 (m, 0.5H), 3.09-3.22 (m, 0.5H), 3.22-3.38 (m, 0.5H), 3.67-3.83 (m, 0.5H), 4.04-4.17 (m, 0.5H), 4.23-4.40 (m, 1H), 4.54-4.65 (m, 0.5H), 4.66-4.83 (m, 1H), 5.58-5.76 (m, 1H), 6.05-6.22 (m, 1H), 6.70-6.96 (m, 1H), 7.32-7.48 (m, 2H), 7.61-7.75 (m, 2H), 8.15-8.26 (brs, 2H), 8.30 (s, 1H)

Reference Example 5

Synthesis of (R)-1-(1-acryloylpiperidin-3-yl)-4-amino-N-(benzo[d]oxazol-2-yl)-1H-pyrazolo[3,4-d]pyrimidine-3-carboxamide.hemi-L-(+)-tartrate (hemitartrate of Compound A)

The Compound A obtained above (600 mg) was dissolved in a mixture of THF (90 mL) and water (60 μL), and in the resultant solution, L-(+)-tartrate (209 mg) was poured and completely dissolved. The solvent was distilled off by azeotropically distilling the mixture with THF twice, to thereby obtain a white solid. Methylethylketone (1.5 mL) was added to this white solid (130 mg) and a heating suspension was carried out at 70° C. for 21 hours. The solid was collected by filtration, then dried under a reduced pressure, and obtained as a white solid. Amount of yield: 96 mg, Ratio of yield: 85.9%

$^1$H-NMR (DMSO-$d_6$): δppm 1.55-1.68 (m, 1H), 1.89-1.97 (m, 1H), 2.10-2.21 (m, 1H), 2.25-2.40 (m, 1H), 2.85-2.95 (m, 0.5H), 3.15-3.65 (m, 1H), 3.68-3.80 (m, 0.5H), 4.05-4.15 (m, 0.5H), 4.24-4.36 (m, 1H), 4.30 (s, 2H), 4.53-4.62 (m, 0.5H), 4.67-4.79 (brs, 1H), 5.67 (dd, J=9.99 Hz, 1H), 6.08-6.18 (m, 1H), 6.71-6.92 (m, 1H), 7.30-7.41 (m, 2H), 7.61-7.73 (m, 2H), 8.22 (brs, 2H), 8.29 (s., 1H)

Reference Example 6

Synthesis of (R)-1-(1-acryloylpiperidin-3-yl)-4-amino-N-(benzo[d]oxazol-2-yl)-1H-pyrazolo[3,4-d]pyrimidine-3-carboxamide.hemi magnesium salt (hemi magnesium salt of Compound A)

To the Compound A obtained above (159.8 mg) was added THF (3 mL) and methanol (1 mL) so as to suspend. Then, 2M aqueous solution of sodium hydroxide (185 μL) was added thereto and the Compound A was completely dissolved therein. Thereafter, magnesium chloride (17.6 mg) was poured therein and the mixture was stirred, to thereby obtain a white solid. After water (2 mL) was added, the solid was collected by filtration. The solid was washed with water (1 mL) twice, and dried under a reduced pressure to thereby obtain a white solid. Methylethylketone (1 mL) was added to this white solid (50 mg) and a heating suspension was carried out at 70° C. for 24 hours. The solid was collected by filtration, then dried under a reduced pressure, and obtained as a white solid. Amount of yield: 44.7 mg, Ratio of yield: 57.3%

$^1$H-NMR (DMSO-$d_6$): δppm 1.52-1.67 (m, 1H), 1.88-2.01 (m, 1H), 2.19-2.41 (m, 2H), 2.75-2.89 (m, 0.5H), 3.07-3.21 (m, 1H), 3.57-3.71 (m, 0.5H), 4.15-4.23 (m, 0.5H), 4.36-4.55 (m, 1H), 4.69-4.88 (m, 2H), 5.60-5.80 (m, 1H), 6.08-6.22 (m, 1H), 6.79-6.96 (m, 1H), 7.08-7.23 (m, 2H), 7.47-7.56 (m, 2H), 8.13-8.22 (brs, 2H), 8.49 (s, 1H), 10.42-10.50 (brs, 1H)

Example 1

Synthesis of (R)-1-(1-acryloylpiperidin-3-yl)-4-amino-N-(benzo[d]oxazol-2-yl)-1H-pyrazolo[3,4-d]pyrimidine-3-carboxamide.monofumarate (monofumarate of Compound A (amorphous))

The Compound A obtained in Reference Example 2 (1.4 g) was dissolved in THF (210 mL) and water (140 µL) at room temperature, and then fumaric acid (376 mg) was poured and completely dissolved therein. The solvent was distilled off with azeotropically distilling the mixture with THF twice, to thereby obtain monofumarate of Compound A (amorphous form) as a white powder. Amount of yield: 1.57 g, Ratio of yield: 90.1%

$^1$H-NMR (DMSO-$d_6$): δppm 1.53-1.68 (m, 1H), 1.86-1.98 (m, 1H), 2.08-2.21 (m, 1H), 2.25-2.39 (m, 1H), 2.82-2.95 (m, 0.5H), 3.10-3.22 (m, 0.5H), 3.23-3.37 (m, 0.5H), 3.68-3.78 (m, 0.5H), 4.04-4.14 (m, 0.5H), 4.22-4.38 (m, 1H), 4.52-4.65 (m, 0.5H), 4.67-4.81 (m, 1H), 5.58-5.74 (m, 1H), 6.03-6.19 (m, 1H), 6.62 (s, 2H), 6.68-6.92 (m, 1H), 7.28-7.40 (m, 2H), 7.59-7.71 (m, 2H), 8.22 (brs, 2H), 8.28 (s, 1H), 12.15 (brs, 1H)

Powder X-ray diffraction spectrum: Shown in FIG. 1.

Example 2

Synthesis of (R)-1-(1-acryloylpiperidin-3-yl)-4-amino-N-(benzo[d]oxazol-2-yl)-1H-pyrazolo[3,4-d]pyrimidine-3-carboxamide.hemifumarate (hemifumarate of Compound A (crystal))

The monofumarate of Compound A obtained in Example 1 (amorphous) (450 mg) was suspended in methylethylketone (27 mL), and a heating suspension was carried out at 80° C. for 24 hours. Through a collection by filtration, and a subsequent drying under a reduced pressure, hemifumarate of Compound A (crystal) was obtained as a white powder. Amount of yield: 279 mg, Ratio of yield: 62.0%

$^1$H-NMR (DMSO-$d_6$): δppm 1.53-1.68 (m, 1H), 1.86-1.98 (m, 1H), 2.08-2.21 (m, 1H), 2.25-2.39 (m, 1H), 2.82-2.95 (m, 0.5H), 3.10-3.22 (m, 0.5H), 3.23-3.37 (m, 0.5H), 3.68-3.78 (m, 0.5H), 4.04-4.14 (m, 0.5H), 4.22-4.38 (m, 1H), 4.52-4.65 (m, 0.5H), 4.67-4.81 (m, 1H), 5.58-5.74 (m, 1H), 6.03-6.19 (m, 1H), 6.62 (s, 1H), 6.68-6.92 (m, 1H), 7.28-7.40 (m, 2H), 7.59-7.71 (m, 2H), 8.22 (brs, 2H), 8.28 (s, 1H), 12.15 (brs, 1H)

Powder X-ray diffraction spectrum: Shown in FIG. 2.
Characteristic diffraction angle (2θ±0.1°): 4.5°, 5.8°, 11.2°, 12.1°, 12.4°, 13.4°, 16.6°, 17.3°, 18.2°, 20.2°, 26.4°, 27.1°

Differential scanning calorie (DSC) curve: Shown in FIG. 3.

Endothermic peak in Differential scanning calorie (DSC) curve: in the vicinity of from 197° C. to 199° C.

Example 3

Synthesis of (R)-1-(1-acryloylpiperidin-3-yl)-4-amino-N-(benzo[d]oxazol-2-yl)-1H-pyrazolo[3,4-d]pyrimidine-3-carboxamide.monofumarate (monofumarate of Compound A (crystal))

The monofumarate of Compound A obtained in Example 1 (amorphous) (500 mg) was suspended in acetonitrile (10 mL), and a heating suspension was carried out at 80° C. for 24 hours. Through a collection by filtration, and a subsequent drying under a reduced pressure, monofumarate of Compound A (crystal) was obtained as a white powder. Amount of yield: 448 mg, Ratio of yield: 89.6%

$^1$H-NMR (DMSO-d): δppm 1.53-1.68 (m, 1H), 1.86-1.98 (m, 1H), 2.08-2.21 (m, 1H), 2.25-2.39 (m, 1H), 2.82-2.95 (m, 0.5H), 3.10-3.22 (m, 0.5H), 3.23-3.37 (m, 0.5H), 3.68-3.78 (m, 0.5H), 4.04-4.14 (m, 0.5H), 4.22-4.38 (m, 1H), 4.52-4.65 (m, 0.5H), 4.67-4.81 (m, 1H), 5.58-5.74 (m, 1H), 6.03-6.19 (m, 1H), 6.62 (s, 2H), 6.68-6.92 (m, 1H), 7.28-7.40 (m, 2H), 7.59-7.71 (m, 2H), 8.22 (brs, 2H), 8.28 (s, 1H), 12.15 (brs, 1H)

Powder X-ray diffraction spectrum: Shown in FIG. 4.
Characteristic diffraction angle (2θ±0.1°): 7.2°, 12.4°, 14.4°, 15.0°, 15.6°, 19.0°, 22.3°, 22.6°, 23.4°, 25.5°, 25.9° and 27.6°

Differential scanning calorie (DSC) curve: Shown in FIG. 5.

Endothermic peak in Differential scanning calorie (DSC) curve: in the vicinity of from 219° C. to 224° C.

Comparative Example 1

Synthesis of (R)-1-(3-(4-amino-3-(4-phenoxyphenyl)-1H-pyrazolo[3,4-d]pyrimidin-1-yl)piperidin-1-yl)prop-2-en-1-one (Comparative compound 1)

Synthesis was carried out in accordance with the method described in WO 2008/121742 pamphlet to obtain the title compound as a white solid.

$^1$H-NMR (DMSO-$d_6$): δppm 1.21-1.28 (m, 1H), 1.42-1.71 (m, 1H), 1.91 (brs, 1H), 2.04-2.36 (m, 2H), 2.91-3.10 (m, 1H), 3.13-3.27 (m, 1H), 3.59-3.76 (m, 1H), 4.04-4.26 (m, 2H), 4.47-4.80 (m, 2H), 5.51-5.78 (m, 1H), 5.96-6.21 (m, 1H), 6.64-6.95 (m, 1H), 7.14 (dd, J=11.46, 8.54 Hz, 6H), 7.40-7.47 (m, 2H), 7.63-7.70 (m, 2H), 8.26 (s, 1H)

Effects of the fumarate of Compound A of the present invention were confirmed by the following Test Examples. In this connection, as the Compound A and the salt thereof of the present Test Examples, crystals thereof were used, unless otherwise described.

Test Example 1

Moisture Absorption/Desorption Test

Moisture absorption/desorption test was carried out with respect to Compound A, monofumarate of Compound A, hemifumarate of Compound A, hemitartrate of Compound A and monophosphate of Compound A, to research the presence or absence of the characteristic of channel hydrate.

In the moisture absorption/desorption test, measurements were carried out according to the following conditions.

A dedicated quartz holder was filled with about from 5 to 10 mg of sample, and a weight of the sample at each humidity was measured and recorded in a continuous manner under the following conditions. Handling of the devices including data processing was based on the method and the process indicated in each device.

Device: VTI SA+ (manufactured by TA Instruments Inc.)

Drying temperature: 60° C.

Temperature rising speed: 1° C./min.

Equilibrium in drying: It is confirmed that no reduction of 0.01 wt % occurs in 5 minutes, in a range not exceeding 300 minutes.

Temperature for measurement: 25° C.

Equilibrium in humidification: It is confirmed that no increase of 0.01 wt % occurs in 5 minutes, in a range not exceeding 120 minutes.

Relative humidity program: Raised by 5% RH from 5% RH to 95% RH, and lowered by 5% RH from 95% RH to 5% RH.

Charts obtained by these tests are shown in FIG. 6 to FIG. 10. The weight changes in the range of measurement condition are shown in Table 2-1 to Table 2-5.

TABLE 2-1

Result of moisture absorption/desorption test of Compound A

| Relative humidity | Weight change ratio (%) | |
|---|---|---|
| (%) | Adsorption | Desorption |
| 5 | 0.42 | 0.67 |
| 20 | 3.08 | 3.20 |
| 40 | 3.60 | 3.65 |
| 60 | 3.88 | 3.88 |
| 80 | 4.09 | 4.11 |
| 95 | 4.39 | 4.39 |

TABLE 2-2

Result of moisture absorption/desorption test of monofumarate of Compound A

| Relative humidity | Weight change ratio (%) | |
|---|---|---|
| (%) | Adsorption | Desorption |
| 5 | 0.01 | 0.05 |
| 20 | 0.14 | 0.17 |
| 40 | 0.30 | 0.33 |
| 60 | 0.37 | 0.41 |
| 80 | 0.45 | 0.49 |
| 95 | 0.60 | 0.60 |

TABLE 2-3

Result of moisture absorption/desorption test of hemifumarate of Compound A

| Relative humidity | Weight change ratio (%) | |
|---|---|---|
| (%) | Adsorption | Desorption |
| 5 | 0.00 | 0.04 |
| 20 | 0.07 | 0.11 |
| 40 | 0.16 | 0.23 |
| 60 | 0.28 | 0.40 |
| 80 | 0.42 | 0.54 |
| 95 | 0.81 | 0.81 |

TABLE 2-4

Result of moisture absorption/desorption test of hemitartrate of Compound A

| Relative humidity | Weight change ratio (%) | |
|---|---|---|
| (%) | Adsorption | Desorption |
| 5 | 0.01 | −0.28 |
| 20 | 1.25 | 1.17 |
| 40 | 1.56 | 1.32 |
| 60 | 1.67 | 1.45 |
| 80 | 1.64 | 1.72 |
| 95 | 3.31 | 3.31 |

TABLE 2-5

Result of moisture absorption/desorption test of monophosphate of Compound A

| Relative humidity | Weight change ratio (%) | |
|---|---|---|
| (%) | Adsorption | Desorption |
| 5 | 0.01 | 5.76 |
| 20 | 0.19 | 8.06 |
| 40 | 0.36 | 9.29 |
| 60 | 0.61 | 10.38 |
| 80 | 1.29 | 12.12 |
| 95 | 17.90 | 17.90 |

As shown in Table 2-1 to Table 2-5, when Compound A was humidified at a relative humidity of from 5 to 95% which is within the range of the measurement condition, the weight change thereof was about 4.4% at a maximum. It was also confirmed that, when the humidity was lowered from the relative humidity of 95%, Compound A almost returned to the original condition. That is, it was found that Compound A had the characteristic of channel hydrate which would absorb/desorb moisture depending on humidity.

Similarly, hemitartrate of Compound A exhibited a weight change of about 3.3% at a maximum, when humidified at a relative humidity of from 5 to 95%. It was also confirmed that, when the humidity was lowered from the relative humidity of 95%, Compound A almost returned to the original condition. That is, it was found that hemitartrate of Compound A also had the characteristic of channel hydrate which would absorb/desorb moisture depending on humidity.

It was also found that, in monophosphate of Compound A, the crystal form after the moisture absorption/desorption test did not maintain the original crystal form.

In contrast, in both the monofumarate of Compound A and hemifumarate of Compound A of the present invention, the mass change was kept at about less than 1% of increase, in the relative humidity of 95%, and it was found that the Compound A almost return to the original condition, when a humidity was lowered. Thus, it was confirmed that the fumarate of Compound A of the present invention is capable of avoiding the characteristic of channel hydrate, and had superior properties as a pharmaceutical product or a drug ingredient for a pharmaceutical product.

Test Example 2

Solid Stability Test (Acceleration Test)

Solid stability was measured under the following conditions, with respect to monofumarate of Compound A, hemifumarate of Compound A, hemitartrate of Compound A and monophosphate of Compound A which were obtained in the Examples and the Reference Examples, when they were stored for 2 weeks or 4 weeks at 40° C./75% RH (sealed condition and opened condition).

Storage condition: 40° C./75% RH (Sealed and Opened) (Opened refers to a condition where a glass container has the lid removed, and is covered with a KimWipe).

Points of measurement: 2 weeks and 4 weeks

Storage amount: About 30 mg

Storage container: Brown glass container

Method of preparing sample solution: Sample was dissolved in 50% acetonitrile such that a concentration of the sample would be 0.4 mg/mL.

Mass of analogous substance in the sample solution was measured by HPLC analysis. Handling of the devices including data processing was based on the method and the process indicated in each device. (Device: Shimadzu Corporation SIL-HTc/LC-20AB)

Column: InertSustein C18, 4.6×150 mm, 3 μm, manufactured by GL Sciences Inc.

MS detection: ESI positive

UV detection: 220 nm

Column temperature: 40° C.

Column flow rate: 1.0 mL/min

Mobile phase: A; 10 mmol/L phosphate buffer (pH 6.0): Acetonitrile mixed solution (17:3), B; Acetonitrile Amount of injection: 5 μL Gradient: Table 3

TABLE 3

| Time (min) | A | B |
|---|---|---|
| 0-18 | 100% to 90% | 0% to 10% |
| 18-30 | 90% to 55% | 10% to 45% |
| 30-35 | 55% to 45% | 45% to 55% |
| 35-45 | 45% | 55% |
| 45-55 | 100% | 0% |

Table 4 shows the results of evaluation on the measured mass of analogous substance. In the Table, A, B and C refer to percentages of the total mass of analogous substance of less than 0.1%, 0.1% or more and less than 0.5%, and 0.5% or more, respectively. Incidentally, those marked with * were measured at 2 weeks' time and the others were measured at 4 weeks' time.

TABLE 4

| | 40° C./75% RH | |
|---|---|---|
| | Opened | Sealed |
| monofumarate of Compound A | A | A |
| hemifumarate of Compound A | A | A |
| hemitartrate of Compound A | B | B |
| monophosphate of Compound A | C* | C* |

As a result of this, it was found that the monofumarate of Compound A and the hemifumarate of Compound A produced small amount of analogous substance, and exhibited excellent solid stabilities compared to the hemitartrate of Compound A or the monophosphate of Compound A. Thus, it was confirmed that the fumarate of Compound A of the present invention exhibits an excellent solid stability.

Test Example 3

Solid Stability Test (Severe Test)

Solid stability was measured under the following conditions, with respect to monofumarate of Compound A, hemitartrate of Compound A and monophosphate of Compound A which were obtained in the Examples and the Reference Examples, when they were stored for 2 weeks or 4 weeks at 60° C.

Storage condition: 60° C. (Sealed)

Point of measurement: 2 weeks and 4 weeks

Storage amount: About 30 mg

Storage container: Brown glass container

Method of preparing sample solution: Sample was dissolved in 50% acetonitrile such that a concentration of the sample would be 0.4 mg/mL.

In the same manner as in Test Example 2, Table 5 shows the results of evaluation on the mass of analogous substance in the sample solution, measured by HPLC analysis. In the Table, A and B refer to percentages of the total mass of analogous substance of less than 0.1%, and 0.1% or more and less than 0.5%, respectively. Incidentally, the value marked with * was measured at 2 weeks and the others were measured at 4 weeks.

TABLE 5

| | 60° C. |
|---|---|
| monofumarate of Compound A | A |
| hemitartrate of Compound A | B |
| monophosphate of Compound A | B* |

As a result, it was found that the monofumarate of Compound A produced small amount of analogous substance, and exhibited excellent solid stabilities compared to the hemitartrate of Compound A or the monophosphate of Compound A. Thus, it was confirmed that the fumarate of Compound A of the present invention exhibits an excellent solid stability.

Test Example 4

Blood Concentration Measurement Test

With respect to Compound A, hemifumarate of Compound A and monofumarate of Compound A obtained in the Examples, suspensions of 50 mg/10 mL/kg in terms of molecular weight of Compound A were prepared with 0.5% HPMC. These administration solutions were orally administered to mice (Balb/cA) which had been bred under a feeding condition, at a dose of 10 mL per 1 kg body weight, with a sonde for oral administration. After the administration, the mice were returned to a cage for mice and conditions were checked. Inside the cage was provided with a condition where water and food were accessible ad libitum. After 0.25, 0.5, 1, 2, 4 and 6 hours from the administration, the mice were anesthetized with isoflurane, and 60 μL of blood was collected from orbital sinus with a capillary blood collection tube.

The collected blood was ice cooled, and blood plasma was separated by a centrifugal operation. The mice after the blood collection was returned to an animal breeding cage, and conditions after recovery from the anesthesia were checked. When the last blood collection was finished, the mice were euthanized by cervical dislocation, after a level check of isoflurane anesthesia.

$AUC_{0-6hr}$, $C_{max}$ and $T_{max}$ were calculated by linear-log trapezoid method with Phoenix WinNonlin (v6.3.0) which is a software manufactured by Pharsight Corporation, from a concentration of Compound A in each blood plasma measured by MRM method with LC-MS/MS.

The results are shown in Table 6. From the test, it was found that with respect to $C_{max}$ (maximum concentration in blood), hemifumarate of Compound A exhibited a value equivalent to that of Compound A, and monofumarate of Compound A exhibited a value about two fold of that of Compound A; and with respect to $AUC_{0-6hr}$ (area under the blood concentration-time curve, 0-6 hours from administration), hemifumarate of Compound A exhibited a value about two fold of that of Compound A, and monofumarate of Compound A exhibited a value about 1.3 times higher than that of Compound A. Thus, it was confirmed that the fumarate of Compound A of the present invention exhibits an excellent oral absorptive property.

TABLE 6

| Parameter | Oral administration | | |
|---|---|---|---|
| | Compound A | monofumarate of Compound A | hemifumarate of Compound A |
| $AUC_{0-6\ hr}$ (µM · hr) | 5.45 | 7.33 | 10.32 |
| $C_{max}$ (µM) | 3.98 | 7.63 | 4.22 |
| $T_{max}$ (h) | 0.25 | 0.25 | 0.5 |

Test Example 5

Measurement of BTK Inhibitory Activity (In Vitro)

In a condition set for a method of measuring inhibitory activity in vitro of the compounds against BTK kinase activity, FL-Peptide 2 was used as a substrate, since it was described in a price list of LabChip (Registered trademark) series sample consumables of PerkinElmer Co., Ltd. that FL-Peptide 2 corresponded to a substrate peptide in a measurement of BTK kinase activity. The refined recombinant human BTK protein used in the test was purchased from Carna Biosciences, Inc.

With regard to the measurement of the inhibitory activity of the compounds, firstly, monofumarate of Compound A was diluted stepwise with dimethyl sulfoxide (DMSO). Subsequently, BTK protein, a substrate peptide (final concentration was 1 µM), magnesium chloride (final concentration was 10 mM), ATP (final concentration was 45 µM), and a DMSO solution of the test compounds (final concentration of DMSO was 5%) were added to a buffer solution for kinase reaction (20 mM HEPES (pH 7.5), 2 mM dithiotheitol, 0.01% Triton X-100), and after the solution was incubated for 40 minutes at 25° C., a kinase reaction was carried out. The reaction was terminated by adding EDTA thereto so as to obtain a final concentration of 30 mM. Finally, a substrate peptide that was not phosphorylated (S) and a phosphorylated peptide (P) were separated and detected by microchannel capillary electrophoresis with a LabChip EZ Reader II (PerkinElmer, Inc.). The amounts of phosphorylation reaction were determined from the individual peak heights of S and P, and the compound concentration at which the phosphorylation reaction could be suppressed by 50% was defined as the IC50 value (nM). The results were shown in Table 7 below.

TABLE 7

| Test compound | BTK inhibitory activity IC50 value (nM) |
|---|---|
| monofumarate of Compound A | 1.19 |

From the test result, it was found that the fumarate of Compound A of the present invention has a BTK inhibitory activity in vitro.

Test Example 6

BTK Inhibition Selectivity Compared with EGFR Kinase Inhibitory Activity (In Vitro)

1) Measurement of BTK Inhibitory Activity

The BTK inhibitory activity was measured in the same manner as in Test Example 5.

2) Measurement of EGFR Inhibitory Activity

With regard to the setting of the conditions for a method for measuring the inhibitory activity of a compound against EGFR kinase activity in vitro, it is described in the consumable reagent supplies price list for LabChip (registered trademark) series of PerkinElmer, Inc. that FL-PEPTIDE 22 corresponds to a substrate peptide for the measurement of EGFR kinase activity. Therefore, a biotinated peptide (biotin-EEPLYWSFPAKKK) was produced by referring to the amino acid sequence of the peptide. The purified recombinant human EGFR protein used in the test was purchased from Carna Biosciences, Inc.

With regard to the measurement of the inhibitory activity of the compounds, firstly, monofumarate of Compound A was diluted stepwise with dimethyl sulfoxide (DMSO). Subsequently, EGFR protein, a substrate peptide (final concentration was 250 nM), magnesium chloride (final concentration was 10 mM), manganese chloride (final concentration was 10 mM), ATP (final concentration was 1.5 µM), and a DMSO solution of the test compounds (final concentration of DMSO was 2.5%) were added to a buffer solution for kinase reaction (20 mM HEPES (pH 7.5), 2 mM dithiotheitol, 0.01% Triton X-100), and after the solution was incubated for 120 minutes at 25° C., a kinase reaction was carried out. The reaction was terminated by adding EDTA thereto so as to obtain a final concentration of 24 mM. Subsequently, a detection liquid containing Eu-labeled anti-phosphotyrosine antibody PT66 (PerkinElmer, Inc.) and SURELIGHT APC-SA (PerkinElmer, Inc.) was added thereto, and the system was left to stand for 2 hours or longer at room temperature. Finally, the amount of fluorescence upon irradiation with excitation light having a wavelength of 337 nm was measured at two wavelengths of 620 nm and 665 nm, with a PHERAstar FS (BMG Labtech GmbH). The amount of phosphorylation reaction was determined from the ratio of the amounts of fluorescence at the two wavelengths, and the compound concentration at which the phosphorylation reaction could be suppressed by 50% was defined as the IC50 value (nM).

3) BTK Inhibition Selectivity

The "EGFR inhibitory activity IC50 value (nM)/BTK inhibitory activity IC50 value (nM)" was calculated based on the results obtained in the above sections 1) and 2), and thereby the BTK inhibition selectivity of the test compound was identified.

TABLE 8

| Test compound | EGFR inhibitory activity IC50 value (nM)/BTK inhibitory activity IC50 value (nM) |
|---|---|
| monofumarate of Compound A | 16.90 |
| Comparative compound 1 | 1.3 |

From the test results, it was found that the BTK inhibition selectivity against EGFR kinase of monofumarate of Compound A of the present invention was about 13 times higher than that of Comparative compound 1 in vitro, and monofumarate of Compound A of the present invention had an excellent BTK inhibition selectivity. From these results, it was demonstrated that the fumarate of Compound A of the present invention could have reduced adverse effects compared with existing BTK inhibitors.

Test Example 7

Test for Measuring Proliferation Inhibitory Activity Against Cell Lines Expressing BTK and EGFR (In Vitro), and Comparison of its Selectivity TMD8 cells, which are of a diffuse large B-cell lymphoma cell line expressing BTK, were suspended in RPMI1640 medium (manufactured by Life Technologies Corp.) containing 10% fetal bovine serum. A431 cells, which are of an EGFR-overexpressing, highly activated human epidermoid carcinoma cell line, were suspended in DMEM, high glucose medium (manufactured by Life Technologies Corp.) containing 10% fetal bovine serum. The cell suspensions were inoculated into each well of 384-well flat-bottomed microplates, and the cells were cultured for 1 day at 37° C. in an incubator containing 5% carbon dioxide gas. The monofumarate of Compound A and Comparative compound 1 were dissolved in DMSO, and the solutions were diluted to a concentration of 500 times the final concentration of the test compound, using DMSO. A DMSO solution of the test compounds was diluted with the medium used in the suspension of the each cell, and this was added to each of the wells of the cell culture plates such that the final concentration of DMSO would be 0.2%. The cells were further cultured for 3 days at 37° C. in an incubator containing 5% carbon dioxide gas. Counting the number of cells before the addition of the compounds and after the culture for 3 days in the presence of the compounds, was carried out with a CELLTITER GLO (manufactured by Promega Corp.) on the basis of the protocol recommended by Promega Corp. The proliferation inhibition ratio was calculated by the following formula, and the concentration of the test compound inhibiting 50% (GI50 (nM)) was determined.

Proliferation inhibition ratio $(\%)=(C-T)/(C-C0)\times 100$

T: Luminescence intensity of a well with the test compound
C: Luminescence intensity of a well without the test compound
C0: Luminescence intensity of a well measured before the addition of the test compound With a comparison between the cell proliferation inhibitory activity against A431 cells that depends on the EGFR proliferation signaling and the cell proliferation inhibitory activity against TMD8 cells that depends on the BTK proliferation signaling, it is possible to evaluate the influence of the respective kinases at a cellular level. That is, by calculating the "A431 cell proliferation inhibition ratio/TMD8 cell proliferation inhibition ratio", it is contemplated that as the value of the ratio is larger, the selectivity to BTK over EGFR in the cells increases. The values of "A431 cell proliferation inhibition ratio/TMD8 cell proliferation inhibition ratio" are shown in Table 9.

TABLE 9

| Test compound | A431 cell proliferation inhibition ratio/TMD8 cell proliferation inhibition ratio |
|---|---|
| monofumarate of Compound A | 7643 |
| Comparative compound 1 | 117.9 |

From the test results, it was found that the BTK inhibition selectivity against EGFR kinase of monofumarate of Compound A of the present invention in the cell proliferation inhibition ratio in vitro was about 65 times as high as that of Comparative compound 1. Thus, it was found that fumarate of Compound A of the present invention had an excellent BTK inhibition selectivity, not only in kinase but also in cells. From the results, it was demonstrated that the fumarate of Compound A of the present invention could reduce adverse effects compared with existing BTK inhibitors.

Test Example 8

Mice Collagen-Induced Arthritis Model (Preventive Effect)

The test was carried out in accordance with the method described in Non-Patent Literature (Brand D D, et al., Nat Protoc. 2007; 2, 1269-1275, Xu D. et al., JPET, 2012 April; 341(1): 90-103). Seven-week-old male/DBA/1 mice (CHARLES RIVER LABORATORIES JAPAN, INC.) were intracutaneously injected in the dorsum with 100 μL/body of an equal amount-mixed solution (emulsion) of 4 mg/mL of bovine type 2 collagen solution (Collagen Research Center) and Complete Freund's Adjuvant (DIFCO Inc.) (initial immunization). After 21 days therefrom, the mice were intracutaneously injected in the chine with 100 μL/body of an equal amount-mixed solution (emulsion) of 4 mg/mL of bovine type 2 collagen solution (Collagen Research Center) and Complete Freund's Adjuvant (DIFCO) to provide an additional immunization. The oral administration of 1 time per day was continued for 17 days setting the administration initiation day (day 0) as the eighth day from the additional immunization. Symptoms of arthritis in day 0, day 3, day 7, day 10, day 14 and day 17 were scored macroscopically (0: No change, 1: Swelling of a finger, 2: Swelling of two fingers or more, 3: Swelling of instep, 4: Swelling of all fingers extending wrist/ankle), and a total in four limbs was obtained as a point of individual body (maximum 16 points). The results are shown in FIG. 11.

Figure 11:
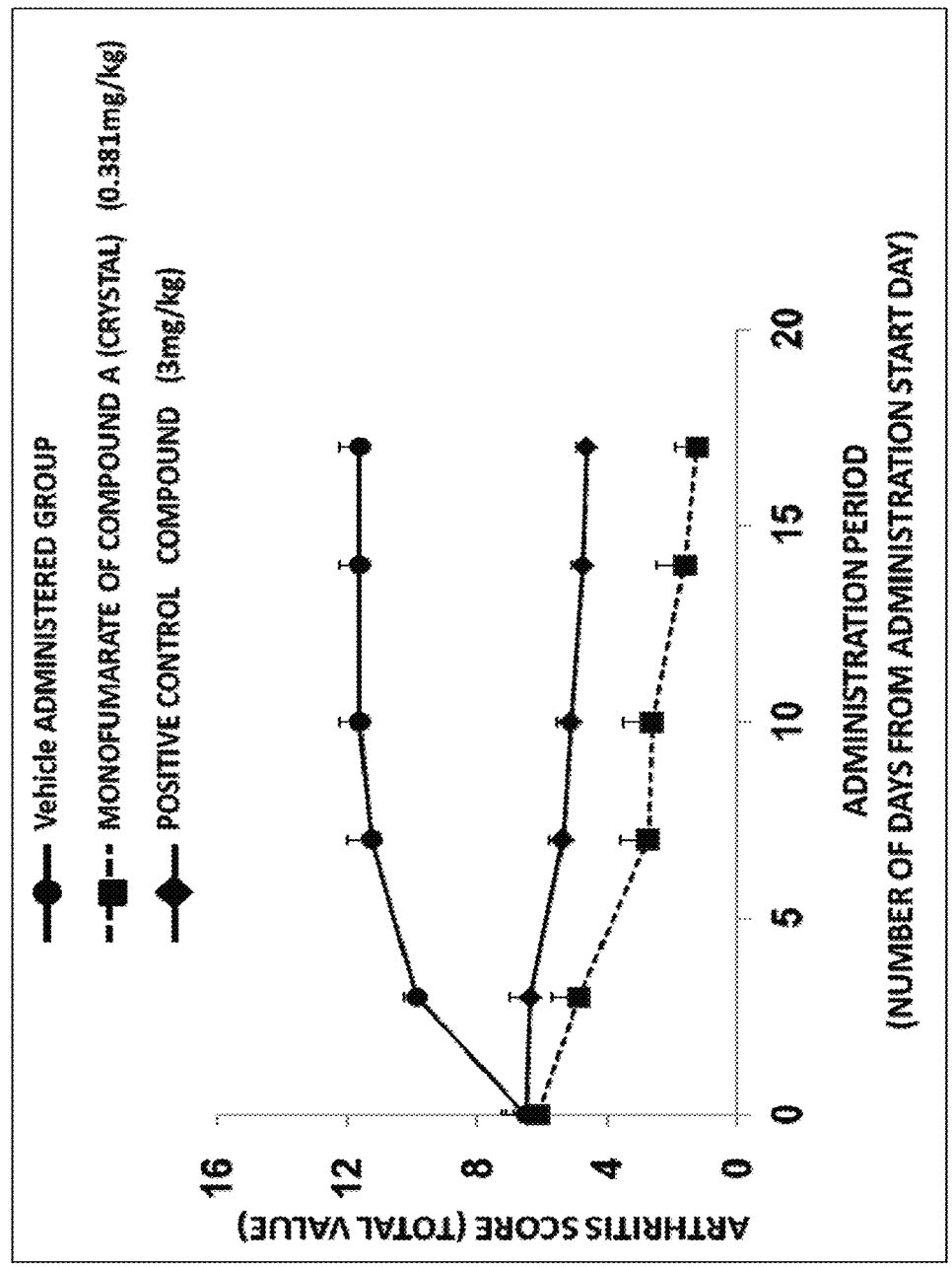
FIG. 11 illustrates an effect of monofumarate of Compound A (crystal) in a mouse collagen-induced arthritis model.

FIG. 11 shows that the group administered with prednisolone (3 mg/kg) which was set as a positive control compound of the test system, was only in a degree of maintaining the raised arthritis score, while the group administered with the monofumarate of Compound A of the present invention (0.381 mg/kg) lowered the arthritis score effectively. From the results, it was confirmed that the fumarate of Compound A of the present invention had an excellent therapeutic effect against rheumatoid arthritis which had already appeared.

The invention claimed is:

1. A fumerate salt, which is (R)-1-(1-acryloylpiperidin-3-yl)-4-amino-N-(benzo[d]oxazol-2-yl)-1H-pyrazolo[3,4-d]pyrimidine-3-carboxamide.hemifumarate.

2. The salt of claim 1, wherein the salt comprises a crystal having a powder X-ray diffraction spectrum having at least eight peaks at diffraction angles (2θ±0.1°) selected from the group consisting of 4.5°, 5.8°, 11.2°, 12.1°, 12.4°, 13.4°, 16.6°, 17.3°, 18.2°, 20.2°, 26.4° and 27.1°.

3. The salt of claim 1, wherein the salt comprises a crystal having a powder X-ray diffraction spectrum having at least five peaks at diffraction angles (2θ±0.1°) selected from the group consisting of 4.5°, 5.8°, 11.2°, 12.1°, 12.4°, 13.4°, 16.6°, 17.3°, 18.2°, 20.2°, 26.4° and 27.1°.

4. The salt of claim 1, wherein the salt comprises a crystal having a powder X-ray diffraction spectrum having peaks at diffraction angles (2θ±0.1°) of 4.5°, 5.8°, 11.2°, 12.1°, 12.4°, 13.4°, 16.6°, 17.3°, 18.2°, 20.2°, 26.4° and 27.1°.

5. The salt of claim 1, wherein the salt comprises a crystal having a powder X-ray diffraction spectrum of FIG. 2.

6. The salt of claim 1, wherein the salt comprises a crystal having a peak temperature in a differential scanning calorie (DSC) curve with an endothermic peak in the vicinity of from 197° C. to 199° C.

7. A fumarate salt which is (R)-1-(1-acryloylpiperidin-3-yl)-4-amino-N-(benzo[d]oxazol-2-yl)-1H-pyrazolo[3,4-d]pyrimidine-3-carboxamide.monofumarate.

8. The salt of claim 7, wherein the salt comprises a crystal having a powder X-ray diffraction spectrum having at least eight peaks at diffraction angles (2θ±0.1°) selected from the group consisting of 7.2°, 12.4°, 14.4°, 15.0°, 15.6°, 19.0°, 22.3°, 22.6°, 23.4°, 25.5°, 25.9° and 27.6°.

9. The salt of claim 7, wherein the salt comprises a crystal having a powder X-ray diffraction spectrum having at least five peaks at diffraction angles (2θ±0.1°) selected from the group consisting of 7.2°, 12.4°, 14.4°, 15.0°, 15.6°, 19.0°, 22.3°, 22.6°, 23.4°, 25.5°, 25.9° and 27.6°.

10. The salt of claim 7, wherein the salt comprises a crystal having a powder X-ray diffraction spectrum having peaks at diffraction angles (2θ±0.1°) of 7.2°, 12.4°, 14.4°, 15.0°, 15.6°, 19.0°, 22.3°, 22.6°, 23.4°, 25.5°, 25.9° and 27.6°.

11. The salt of claim 7, wherein the salt comprises a crystal having a powder X-ray diffraction spectrum of FIG. 4.

12. The salt of claim 7, wherein the salt comprises a crystal having a peak temperature in a differential scanning calorie (DSC) curve with an endothermic peak in the vicinity of from 219° C. to 224° C.

13. The salt of claim 7, wherein the salt comprises an amorphous solid exhibiting a halo pattern in a powder X-ray diffraction spectrum.

14. The salt of claim 7, wherein the salt comprises an amorphous solid having a powder X-ray diffraction spectrum of FIG. 1.

15. A pharmaceutical composition, comprising:
the salt of claim 1; and
a pharmaceutical carrier.

* * * * *